(12) United States Patent
Campbell et al.

(10) Patent No.: US 8,684,904 B2
(45) Date of Patent: Apr. 1, 2014

(54) BLOOD PUMP WITH EXPANDABLE CANNULA

(71) Applicants: Thoratec Corporation, Pleasanton, CA (US); The Penn State Research Foundation, University Park, PA (US)

(72) Inventors: Robert L. Campbell, Port Matilda, PA (US); Justin M. Walsh, Spring Mills, PA (US); Daniel Metrey, Port Matilda, PA (US); Robert F. Kunz, State College, PA (US); Thomas M. Mallison, State College, PA (US); Edward Boone, Pennsylvania Furnace, PA (US); Eric Myer, Spring Mills, PA (US); Mark W. McBride, Bellefonte, PA (US); Kevin J. Powell, Glen Gardner, NJ (US); Daniel A. Walters, Rockaway Township, NJ (US)

(73) Assignees: Thoratec Corporation, Pleasanton, CA (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/968,161

(22) Filed: Aug. 15, 2013

(65) Prior Publication Data
US 2013/0331639 A1 Dec. 12, 2013

Related U.S. Application Data

(63) Continuation of application No. 12/829,359, filed on Jul. 1, 2010, now Pat. No. 8,535,211.

(60) Provisional application No. 61/222,236, filed on Jul. 1, 2009.

(51) Int. Cl.
*A61N 1/362* (2006.01)
*A61N 1/00* (2006.01)

(52) U.S. Cl.
USPC ............. 600/16; 607/46; 607/59; 607/60

(58) Field of Classification Search
USPC .................. 600/16; 607/46, 59–60
See application file for complete search history.

(56) References Cited

U.S. PATENT DOCUMENTS

| 1,902,418 A | 3/1933 | Pilgrim |
| 2,356,659 A | 10/1942 | Aguiar |

(Continued)

FOREIGN PATENT DOCUMENTS

| CA | 2367469 | 10/2000 |
| CA | 2407938 | 11/2002 |

(Continued)

OTHER PUBLICATIONS

ABIOMED, "Impella 5.0 with the Impella Console, Circulatory Support System, Instructions for Use & Clinical Reference Manual," Jun. 2010, in 122 pages.

(Continued)

*Primary Examiner* — Nicole F Lavert
(74) *Attorney, Agent, or Firm* — Knobbe Martens Olson & Bear LLP

(57) ABSTRACT

A blood pump includes an impeller having a plurality of foldable blades and a cannula having a proximal portion with a fixed diameter, and a distal portion with an expandable diameter. The impeller can reside in the expandable portion of the cannula. The cannula has a collapsed condition for percutaneous delivery to a desired location within the body, and an expanded condition in which the impeller can rotate to pump blood. A flexible drive shaft can extend through the cannula for rotationally driving the impeller within the patient's body.

29 Claims, 14 Drawing Sheets

(56) References Cited

U.S. PATENT DOCUMENTS

| | | |
|---|---|---|
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Donaldson |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,129,129 A | 12/1978 | Amrine |
| 4,135,253 A | 1/1979 | Reich et al. |
| 4,149,535 A | 4/1979 | Volder |
| 4,304,524 A | 12/1981 | Coxon et al. |
| 4,382,199 A | 5/1983 | Isaacson |
| 4,392,836 A | 7/1983 | Sugawara |
| 4,458,366 A | 7/1984 | MacGregor |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,686,982 A | 8/1987 | Nash |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffmann et al. |
| 5,021,048 A | 6/1991 | Buckholtz |
| 5,049,134 A | 9/1991 | Golding et al. |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,349 A | 5/1992 | Summers et al. |
| 5,129,883 A | 7/1992 | Black |
| 5,147,186 A | 9/1992 | Buckholtz |
| 5,163,910 A | 11/1992 | Schwartz et al. |
| 5,171,212 A | 12/1992 | Buck et al. |
| 5,190,528 A | 3/1993 | Fonger et al. |
| 5,201,679 A | 4/1993 | Velte et al. |
| 5,211,546 A | 5/1993 | Isaacson et al. |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,376,114 A | 12/1994 | Jarvik |
| 5,393,207 A | 2/1995 | Maher et al. |
| 5,405,383 A | 4/1995 | Barr |
| 5,437,541 A | 8/1995 | Vainrub |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,534,287 A | 7/1996 | Lukic |
| 5,588,812 A | 12/1996 | Taylor et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,707,218 A | 1/1998 | Maher et al. |
| 5,722,930 A | 3/1998 | Larson et al. |
| 5,730,628 A | 3/1998 | Hawkins |
| 5,738,649 A | 4/1998 | Macoviak |
| 5,741,234 A | 4/1998 | Aboul-Hosn |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,868,702 A | 2/1999 | Stevens |
| 5,868,703 A | 2/1999 | Bertolero |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,964,694 A | 10/1999 | Siess et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,056,719 A | 5/2000 | Mickley |
| 6,058,593 A | 5/2000 | Siess |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,200,260 B1 | 3/2001 | Bolling |
| 6,210,133 B1 | 4/2001 | Aboul-Hosn et al. |
| 6,210,397 B1 | 4/2001 | Aboul-Hosn et al. |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,295,877 B1 | 10/2001 | Aboul-Hosn et al. |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,503,224 B1 | 1/2003 | Forman et al. |
| 6,508,777 B1 | 1/2003 | Macoviak et al. |
| 6,508,787 B2 | 1/2003 | Erbel et al. |

(56) References Cited

U.S. PATENT DOCUMENTS

| | | |
|---|---|---|
| 6,517,315 B2 | 2/2003 | Belady |
| 6,517,528 B1 | 2/2003 | Pantages et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | de Blanc et al. |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,641,558 B1 | 11/2003 | Aboul-Hosn et al. |
| 6,660,014 B2 | 12/2003 | Demarais et al. |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,783,328 B2 | 8/2004 | Lucke et al. |
| 6,790,171 B1 | 9/2004 | Grundeman et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,860,713 B2 | 3/2005 | Hoover |
| 6,866,625 B1 | 3/2005 | Ayre et al. |
| 6,866,805 B2 | 3/2005 | Hong et al. |
| 6,889,082 B2 | 5/2005 | Bolling et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,229,258 B2 | 6/2007 | Wood et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,284,956 B2 | 10/2007 | Nose et al. |
| 7,288,111 B1 | 10/2007 | Holloway et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride |
| 7,491,163 B2 | 2/2009 | Viole et al. |
| 7,534,258 B2 | 5/2009 | Gomez |
| 7,605,298 B2 | 10/2009 | Bechert et al. |
| 7,619,560 B2 | 11/2009 | Penna |
| 7,682,673 B2 | 3/2010 | Houston et al. |
| 7,731,675 B2 | 6/2010 | Aboul-Hosn et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,819,833 B2 | 10/2010 | Ainsworth et al. |
| 7,828,710 B2 | 11/2010 | Shifflette |
| 7,841,976 B2 | 11/2010 | McBride et al. |
| 7,927,068 B2 | 4/2011 | McBride et al. |
| 7,942,804 B2 | 5/2011 | Khaw |
| 7,942,844 B2 | 5/2011 | Moberg et al. |
| 7,993,259 B2 | 8/2011 | Kang et al. |
| 7,998,054 B2 | 8/2011 | Bolling |
| 8,012,079 B2 | 9/2011 | Delgado |
| 8,079,948 B2 | 12/2011 | Shifflette |
| 8,110,267 B2 | 2/2012 | Houston et al. |
| 8,114,008 B2 | 2/2012 | Hidaka et al. |
| 8,177,703 B2 | 5/2012 | Smith et al. |
| 8,206,350 B2 | 6/2012 | Mann et al. |
| 8,277,470 B2 | 10/2012 | Demarais et al. |
| 8,364,278 B2 | 1/2013 | Pianca et al. |
| 8,376,707 B2 | 2/2013 | McBride et al. |
| 8,439,859 B2 | 5/2013 | Pfeffer et al. |
| 8,485,961 B2 | 7/2013 | Campbell et al. |
| 8,535,211 B2 | 9/2013 | Campbell et al. |
| 2002/0111663 A1 | 8/2002 | Dahl et al. |
| 2002/0151761 A1 | 10/2002 | Beizai et al. |
| 2002/0169413 A1 | 11/2002 | Keren et al. |
| 2003/0018380 A1 | 1/2003 | Craig et al. |
| 2003/0100816 A1 | 5/2003 | Siess |
| 2003/0135086 A1 | 7/2003 | Khaw et al. |
| 2003/0187322 A1 | 10/2003 | Siess et al. |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2004/0019251 A1 | 1/2004 | Viole et al. |
| 2004/0044266 A1 | 3/2004 | Siess et al. |
| 2004/0101406 A1 | 5/2004 | Hoover |
| 2004/0113502 A1 | 6/2004 | Li et al. |
| 2004/0236173 A1 | 11/2004 | Viole et al. |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0095124 A1 | 5/2005 | Arnold et al. |
| 2005/0113631 A1 | 5/2005 | Bolling et al. |
| 2005/0135942 A1 | 6/2005 | Wood et al. |
| 2005/0165269 A9 | 7/2005 | Aboul-Hosn et al. |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0156006 A1 | 7/2007 | Smith et al. |
| 2007/0203442 A1 | 8/2007 | Bechert et al. |
| 2007/0208298 A1 | 9/2007 | Ainsworth et al. |
| 2007/0233270 A1 | 10/2007 | Weber et al. |
| 2007/0282417 A1 | 12/2007 | Houston et al. |
| 2008/0004690 A1 | 1/2008 | Robaina |
| 2008/0031953 A1 | 2/2008 | Takakusagi et al. |
| 2008/0103442 A1 | 5/2008 | Kesten et al. |
| 2008/0103591 A1 | 5/2008 | Siess |
| 2008/0114339 A1 | 5/2008 | McBride et al. |
| 2008/0132748 A1 | 6/2008 | Shifflette |
| 2008/0167679 A1 | 7/2008 | Papp |
| 2008/0275290 A1 | 11/2008 | Viole et al. |
| 2008/0306327 A1 | 12/2008 | Shifflette |
| 2009/0023975 A1 | 1/2009 | Marseille et al. |
| 2009/0062597 A1 | 3/2009 | Shifflette |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2010/0087773 A1 | 4/2010 | Ferrari |
| 2010/0127871 A1 | 5/2010 | Pontin |
| 2010/0191035 A1 | 7/2010 | Kang et al. |
| 2010/0197994 A1 | 8/2010 | Mehmanesh |
| 2010/0210895 A1 | 8/2010 | Aboul-Hosn et al. |
| 2010/0286210 A1 | 11/2010 | Murata et al. |
| 2011/0004291 A1 | 1/2011 | Davis et al. |
| 2011/0021865 A1 | 1/2011 | Aboul-Hosn et al. |
| 2011/0034874 A1 | 2/2011 | Reitan |
| 2011/0071338 A1 | 3/2011 | McBride et al. |
| 2011/0076439 A1 | 3/2011 | Zeilon |
| 2011/0236210 A1 | 9/2011 | McBride et al. |

(56) References Cited

U.S. PATENT DOCUMENTS

| | | |
|---|---|---|
| 2011/0257462 A1 | 10/2011 | Rodefeld |
| 2011/0270182 A1 | 11/2011 | Breznock et al. |
| 2012/0004495 A1 | 1/2012 | Bolling |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2013/0129503 A1 | 5/2013 | McBride et al. |

FOREIGN PATENT DOCUMENTS

| | | |
|---|---|---|
| CA | 2480467 | 8/2003 |
| DE | 196 13 565 | 10/1997 |
| EP | 0 364 293 | 10/1989 |
| EP | 0 453 234 | 10/1991 |
| EP | 0 533 432 | 9/1992 |
| EP | 1207934 | 5/2002 |
| EP | 2151257 | 2/2010 |
| EP | 2263732 | 12/2010 |
| FR | 2267800 | 4/1974 |
| JP | S48-23295 | 3/1973 |
| JP | S58-190448 | 7/1983 |
| JP | H06-114101 | 4/1994 |
| JP | H08-500512 | 1/1996 |
| JP | H08-501466 | 2/1996 |
| JP | 10-099447 | 4/1998 |
| JP | 2002-505168 | 2/2002 |
| JP | 2004-514506 | 5/2004 |
| JP | 2011-000620 | 9/2005 |
| JP | 2011-157961 | 8/2011 |
| WO | WO 89/04644 | 6/1989 |
| WO | WO 89/05164 | 6/1989 |
| WO | WO 94/05347 | 3/1994 |
| WO | WO 94/06486 | 3/1994 |
| WO | WO 97/15228 | 5/1997 |
| WO | WO 97/37697 | 10/1997 |
| WO | WO 99/00368 | 1/1999 |
| WO | WO 99/16387 | 4/1999 |
| WO | WO 99/37352 | 7/1999 |
| WO | WO 99/44651 | 9/1999 |
| WO | WO 99/44670 | 9/1999 |
| WO | WO 99/59652 | 11/1999 |
| WO | WO 00/12148 | 3/2000 |
| WO | WO 00/18448 | 4/2000 |
| WO | WO 00/19097 | 4/2000 |
| WO | WO 00/41612 | 7/2000 |
| WO | WO 00/43053 | 7/2000 |
| WO | WO 00/45874 | 8/2000 |
| WO | WO 00/61207 | 10/2000 |
| WO | WO 00/69489 | 11/2000 |
| WO | WO 01/24867 | 4/2001 |
| WO | WO 01/83016 | 11/2001 |
| WO | WO 02/070039 | 9/2002 |
| WO | WO 03/048582 | 6/2003 |
| WO | WO 03/068303 | 8/2003 |
| WO | WO 03/070299 | 8/2003 |
| WO | WO 03/103745 | 12/2003 |
| WO | WO 2005/089674 | 9/2005 |
| WO | WO 2005/123158 | 12/2005 |
| WO | WO 2006/034158 | 3/2006 |
| WO | WO 2006/051023 | 5/2006 |
| WO | WO 2007/112033 | 10/2007 |
| WO | WO 2008/034068 | 3/2008 |
| WO | WO 2009/073037 | 6/2009 |
| WO | WO 2010/127871 | 11/2010 |
| WO | WO 2010/149393 | 12/2010 |
| WO | WO 2011/003043 | 1/2011 |
| WO | WO 2011/035926 | 3/2011 |
| WO | WO 2011/035929 | 3/2011 |
| WO | WO 2011/076439 | 6/2011 |
| WO | WO 2011/089022 | 7/2011 |
| WO | WO 2012/007140 | 1/2012 |
| WO | WO 2012/007141 | 1/2012 |

OTHER PUBLICATIONS

International Search Report and Written Opinion received in International Patent Application No. PCT/US2013/040798, mailed on Aug. 21, 2013, in 16 pages.
International Search Report and Written Opinion received in International Patent Application No. PCT/US2013/040799, mailed on Aug. 21, 2013, in 19 pages.
International Search Report and Written Opinion received in International Patent Application No. PCT/US2013/040809, mailed on Sep. 2, 2013, in 25 pages.
Inernational Search Report received in International Patent Application No. PCT/US2003/004401, mailed on Nov. 10, 2003, in 9 pages.
International Search Report and Written Opinion received in International Patent Application No. PCT/US2013/048343, mailed on Oct. 11, 2013, in 15 pages.
International Search Report and Written Opinion received in International Patent Application No. PCT/US2013/048332, mailed on Oct. 16, 2013, in 17 pages.
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
ABIOMED—Recovering hearts. Saving lives., Impella 2.5 System, Instructions for Use, Jul. 2007, 86 sheets.
Barras CDJ, Myers KA. Nitinol—Its Use in vascular Surgery and Other Applications. Eur J. Vasc Endovasc Surg 2000; 19:564-9.
Biscarini A., Mazzolai G., Tuissi A., "Enhanced nitinol properties for biomedical applications," Recent Patents on Biomedical Engineering 2008; 1(3): 180-96.
Cardiovascular Diseases (CVDs) Fact Sheet No. 317. World Health Organization. [Online] Sep. 2011. http://www.who.int/mediacentre/factsheets/fs317/en/index.html, accessed on Aug. 29, 2012.
Duerig T, Pelton A, Stockel D. "An Overview of nitinol Medical Applications," Mat Sci Eng 1999: 149-160.
Extended European Search Report received from the European Patent Office in European Patent Application No. EP 07753903.9, dated Oct. 8, 2012, 7 pages.
European Search Report received from the European Patent Office in EP Application No. EP 05799883.3 dated May 10, 2011, 4 pages.
Grech ED. Percutaneous coronary intervention. I: History and development. BMJ. 2003;326:1080-.
Hsu et al. "Review of Recent Patents on Foldable Ventricular Assist Devices," Recent Patents on Biomedical Engineering, 2012, pp. 208-222, vol. 5.
International Search Report received in PCT Application No. PCT/US2003/04853, mailed Jul. 3, 2003, 3 pages.
International Search Report and Written Opinion received in PCT Application No. PCT/US2012/020382, mailed Jul. 31, 2013.
International Search Report and Written Opinion received in PCT Application No. PCT/US2012/020369 mailed Jul. 30, 2012.
International Search Report and Written Opinion received in PCT Application No. PCT/US2012/020553 mailed Aug. 17, 2012.
International Search Report and Written Opinion received in PCT Application No. PCT/US2012/020383 mailed Aug. 17, 2012.
Written Opinion received in PCT Application No. PCT/US2003/04853, dated Feb. 25, 2004, 5 pages.
International Preliminary Examination Report from the European Patent Office received in PCT Application No. PCT/US2003/04853, mailed Jul. 26, 2004, 5 pages.
International Search Report received in PCT Application No. PCT/US2003/04401, mailed Nov. 10, 2003, 9 pages.
International Preliminary Examination Report from the European Patent Office received in PCT Application No. PCT/US2003/04401, mailed May 18, 2004, 4 pages.
International Search Report and Written Opinion received in PCT Application No. PCT/US2005/33416, mailed Dec. 11, 2006, 8 pages.
International Preliminary Report on Patentability and Written Opinion of the International Searching Authority received in PCT Application No. PCT/US2005/033416, mailed Mar. 20, 2007, 7 pages.

(56) References Cited

OTHER PUBLICATIONS

Krishnamani R, DeNofrio D, Konstam MA. Emerging ventricular assist devices for long-term cardiac support. Nat Rev Cardiol 2010; 7-71-6.

Morgan NB. "Medical Shape memory alloy applications—the market and its products," Mat Sci Eng 2004; 378:16-23.

Petrini L, Migliavacca F. Biomedical Applications of Shape Memory Alloys. Journal of Metallurgy 2011.

Raess D, Weber D. Impella 2.5 J. Cardiovasc Transl Res 2009; 2 (2): 168-72.

Reitan, Oyvind, et al., Hemodynamic Effects of a New Percutaneous Circulatory Support Device in a Left Ventricular Failure Model. ASAIO Journal 2003: 49:731-6.

Smith EJ, et al. "First-In-Man Study of the Reitan Catheter Pump for circulatory Support in Patients Undergoing High-Risk Percutaneous Coronary Intervention." Catheter Cardiovasc Interv 2009; 73(7):859-65.

Sokolowski W., Metcalfe A., Hayashi S., Yuahia L., Raymond K., "Medical Applications of Shape Memory Polymers." Biomed Mater 2007;2(1):S23-S27.

"Statistical Analysis and Clinical Experience with the Recover® Pump Systems", Impella CardioSystems GmbH, 2 sheets.

Stoeckel D, Pelton A, Duerig T. Self-Expanding nitinol stents: material and design considerations. European Radiology. 2004; 14:292-301.

Supplementary European Search Report received from the European Patent Office in EP Application No. EP 05799883 dated Mar. 19, 2010, 3 pages.

International Search Report and Written Opinion received in PCT Application No. PCT/US2007/07313, mailed Mar. 4, 2008, 6 pages.

International Preliminary Report on Patentability of the International Searching Authority received in PCT Application No. PCT/US2007/007313, mailed Sep. 23, 2008, 6 pages.

International Search Report and Written Opinion received in PCT Application No. PCT/US2010/040847 mailed on Dec. 14, 2010, 17 pages.

Ide, Hirofumi et al., Hemodynamic Evaluation of a New Left Ventricular Assist Device, Artificial Organs 16 (3): 286-290; 1992.

Ide, Hirofumi et al., Evaluation of the Pulsatility of a New Pulsatile Left Ventricular Assist Device—the Integrated Cardioassist Catheter—in Dogs, J. of Cardiovascular Surgery 107 (2): 569-0575; Feb. 1994.

Mihaylov , D. et al., Evaluation of the Optimal Driving Mode During Left Ventricular Assist with Pulsatile Catheter Pump in Calves, Artificial Organs 23(12): 1117-1122; 1999.

Mihaylov, Dimiter et al., Development of a New Introduction Technique for the Pulsatile Catheter Pump, Artificial Organs 21(5): 425-427; 1997.

Morsink, PLJ et al., Numerical Modelling of Blood Flow Behaviour in the Valved Catheter of the PUCA Pump, a LVAD, The International Journal of Artificial Organs 20(5): 277-284; 1997.

Nishimura et al. The enabler cannula pump: a novel circulatory support system. The International Journal of Artificial Organs, vol. 22, No. 5, 1999, pp. 317-323.

Rakhorst, Gerhard et al., In Vitro Evaluation of the Influence of Pulsatile Intraventricular Pumping on Ventricular Pressure Patterns, Artificial Organs 18(7): 494-499; 1994.

Reitan, Oyvind, et al., Hydrodynamic Properties of a New Percutaneous Intra-aortic Axial Flow Pump. ASAIO Journal 2000. pp. 323-328.

Schmitz-Rode, Thomas et al., "An Expandable Percutaneous Catheter Pump for Left Ventricular Support", Journal of the American College of Cardiology, vol. 45, No. 11, 2005, pp. 1856-1861.

Sharony, R. et al. Right heart support during off-pump coronary artery surgery—a multi-center study. Heart Surg Forum. 2002;5(1):13-16.

Sharony et al. Cardiopulmonary Support and Physiology—The Intra-Aortic Cannula Pump: A Novel Assist Device for the Acutely Failing Heart. The Journal of Thoracic and Cardiovascular Surgery, Nov. 1992, vol. 118, No. 5, pp. 924-929.

Takagaki et al. A Novel Miniature Ventricular Assist Device for Hemodynamic Support. ASAIO Journal 2001, pp. 412-416.

Throckmorton A., et al., "Flexible Impeller Blades in an Axial Flow Pump for Intravascular Cavopulmonary Assistance of the Fontan Physiology." Cardiovasc Eng Technology 2010; 1(4): 244-55.

Verkerke, Gijsbertus et al., Numerical Simulation of the Pulsating Catheter Pump: A Left Ventricular Assist Device, Artificial Organs 23(10): 924-931; 1999.

Verkerke, Bart et al., The PUCA Pump: A Left Ventricular Assist Device, Artificial Organs 17(5): 365-368; 1993.

Verkerke, CJ et al., Numerical Simulation of the PUCA Pump, A Left Ventricular Assist Device, Abstracts of the XIXth ESAO Congress, The International Journal of Artificial Organs 15(9): 543; 1992.

Wampler, Richard. K., et al., The Sternotomy Hemopump, A Second Generation Intraarterial Ventricular Assist Device; Johnson and Johnson Interventional Systems, pp. M218-M223, 1993.

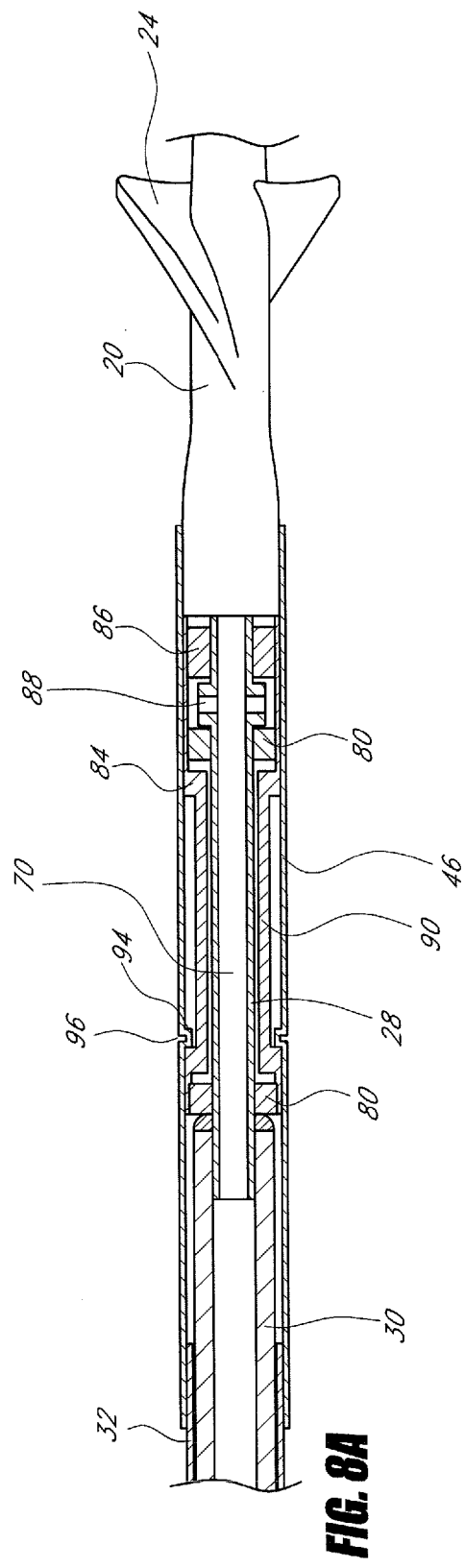
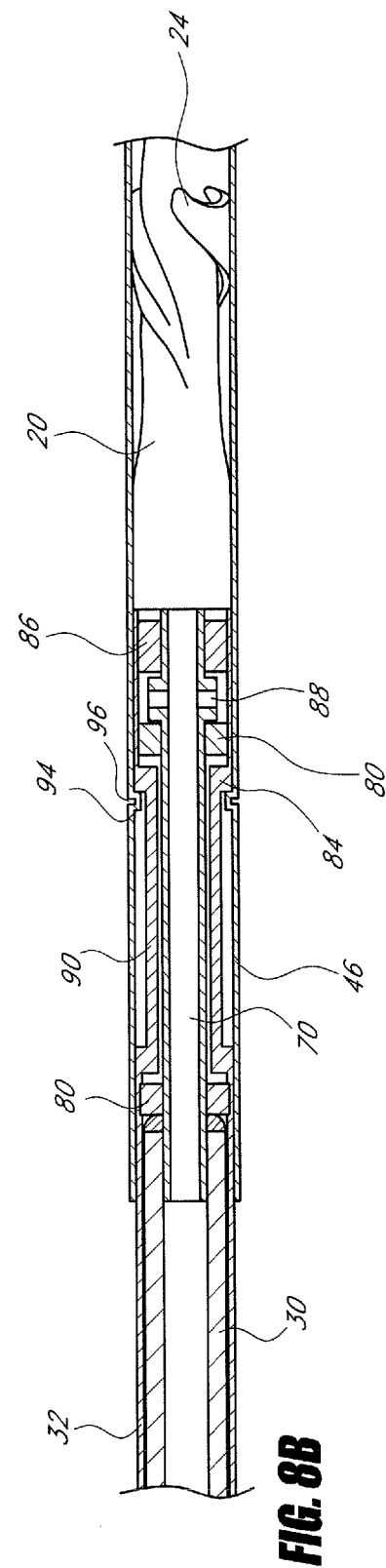
FIG. 8A
FIG. 8B ial Patent Application Ser. No. 61/222,236, filed Jul. 1, 2009, each of which is incorporated herein by reference in its entirety for all purposes.

BLOOD PUMP WITH EXPANDABLE CANNULA

CROSS-REFERENCE TO RELATED APPLICATIONS

This application is a continuation of U.S. patent application Ser. No. 12/829,359, which is now U.S. Pat. No. 8,535,211, issued on Sep. 17, 2013, which claims priority to U.S. Provisional Patent Application Ser. No. 61/222,236, filed Jul. 1, 2009, each of which is incorporated herein by reference in its entirety for all purposes.

BACKGROUND OF THE INVENTION

1. Field of the Invention

This application relates to blood pumps such as left or right ventricular assist devices with an expandable impeller for treatment of heart disease. Still more particularly, this application relates to expandable cannulas for use in such blood pumps, and to other structural features of these devices.

2. Description of the Related Art

Heart disease is a major problem in society, and claims many lives per year. After a heart attack, only a small number of patients can be treated successfully and non-invasively using medicines, such as pharmaceuticals. However, with sufficient mechanical assistance to the heart function, a majority of patients may recover from a heart attack, including those with cardiogenic shock.

In a conventional approach, a blood pump having a fixed cross-section is surgically inserted within the left ventricle of the heart and the aortic arch to assist the heart in its function. Surgical placement is required, since it is presently impractical or impossible to percutaneously insert a pump of the size needed for sustaining adequate blood flow. The object of the surgically inserted pump is to reduce the load on the heart muscle for a period of time, which may be as long as a week, allowing the affected heart muscle to recover while healing in a substantially unloaded state.

Surgical insertion, however, can cause additional serious stresses in heart failure patients. Accordingly, devices have been developed which are capable of percutaneous insertion while at the same time providing an adequate amount of blood flow. Such devices, including those described in U.S. Pat. No. 7,393,181 and pending Application No. 11/728,051, the disclosures of which are hereby incorporated by reference herein, have a sufficiently small diameter to be inserted percutaneously through a femoral artery, but may subsequently be expanded in diameter so as to generate a sufficient sustaining blood flow.

SUMMARY OF THE INVENTION

The operation of the aforementioned percutaneous blood pumps have faced several challenges, including the leakage of blood through a guide wire lumen extending through the pump impeller, maintaining the blood pump impeller centered within the outer cannula as the cannula bends within the vascular system, retracting the blood pump into the insertion sheath for removal from the human body, and designing and maintaining the shape of the expandable portion of the cannula of the blood pump to optimize performance.

There exists a need for improvements to expandable blood pumps which address all of the foregoing problems so as to improve overall performance. The inventions disclosed herein address one or more of these and other needs.

In some embodiments, an apparatus for inducing motion of a fluid relative to the apparatus is provided. The apparatus can include an elongated cannula having a proximal portion and a distal portion, the proximal portion including a conduit having a fixed diameter, and the distal portion including an expandable portion having a diameter expandable to a diameter greater than the fixed diameter. The apparatus can also include an impeller positioned in the elongated cannula and having a deployed configuration and a stored configuration.

The impeller can include a hub and a passageway extending through the hub between a first end and a second end. A valve can be positioned in the hub. The valve can have a first condition for occluding flow of a first fluid through the passageway from the first end to the second end, and a second condition for occluding flow of a second fluid through the passageway from the second end to the first end.

In certain embodiments, a blade is supported by the hub, the blade having a proximal end attached to the hub and a distal end. In a deployed configuration of the impeller, the blade extends away from the hub. In a stored configuration of the impeller, the blade can be compressed so as to move the distal end of the blade towards the hub.

In some embodiments, of the apparatus for inducing motion of a fluid, the apparatus includes a vane assembly positioned in the expandable portion of the cannula distally of the impeller and having a deployed configuration and a stored configuration. The vane assembly includes a vane hub and a plurality of vanes supported by the vane hub. Each of the vanes has a proximal end attached to the vane hub and a distal end. The vanes, in the deployed configuration of the vane assembly, extend away from the vane hub. In the stored configuration, the vanes of the vane assembly are compressed so as to move the distal ends of the vanes towards the vane hub. The vane assembly can be connected to the impeller so that the vane assembly moves with the impeller in a longitudinal direction of the elongated cannula and so that the vane assembly does not rotate with the impeller.

In other embodiments of the apparatus for inducing motion of a fluid, the expandable portion of the cannula has an inlet end, an outlet end and a diameter expandable to a diameter greater than the fixed diameter. The expandable portion includes a generally tubular reinforcing matrix, a layer of a first polymer at least partially coating an exterior of the reinforcing matrix and a layer of a second polymer different from the first polymer. The second polymer layer can be located in a region adjacent the inlet end of the expandable portion.

In some embodiments, the apparatus for inducing motion of a fluid includes an elongated cannula having a proximal portion and a distal portion. The proximal portion includes an expandable portion having a generally tubular reinforcing matrix with a plurality of circumferential rings each having an undulating pattern. The undulating pattern can include a plurality of apexes pointing toward the inlet end and a plurality of recesses pointing toward the outlet end. The undulating pattern can also include a plurality of apexes pointing toward the outlet end and a plurality of recesses pointing toward the inlet end. The matrix can also include a plurality of connectors. For example, the connectors can connect the apices pointing toward the outlet end in one of the rings to an adjacent one of the rings.

In other embodiments of the apparatus for inducing motion of a fluid relative to the apparatus, an expandable portion of a cannula is provided that has an inlet end, an outlet end and a diameter expandable to a diameter greater than the fixed diameter. The expandable portion includes a generally tubular reinforcing matrix and a layer of a first polymer at least partially coating an exterior of the reinforcing matrix. The reinforcing matrix includes a plurality of circumferential rings each having an undulating pattern including a first plurality of apices pointing toward the inlet end and defining a first plurality of recesses pointing toward the outlet end. Each circumferential ring can also include a second plurality of apices pointing toward the outlet end and defining a second plurality of recesses pointing toward the inlet end. At least one region of a second polymer different from the first polymer overlies the first polymer layer and connects one of the apices pointing toward the outlet end in one of the rings to at least one other ring.

Another aspect of the present invention provides a pump for pumping fluid at a desired location. In accordance with one embodiment hereof, the pump includes a cannula having a compact state for insertion to the desired location and an expanded state; an impeller positioned within the cannula and having a hub and a plurality of blades supported by the hub, the hub including a passageway extending between a first end and a second end, each blade having a proximal end attached to the hub and a distal end, the impeller having a stored configuration and a deployed configuration; a valve positioned in the hub and having a first condition for occluding flow of a first fluid through the passageway from the first end to the second end, and having a second condition for occluding flow of a second fluid through the passageway from the second end to the first end; and a drive mechanism for rotating the impeller in the deployed configuration. The blades in the stored configuration of the impeller are compressed so as to move the distal ends of the blades towards the hub, and the blades in the deployed configuration of the impeller extend away from the hub. The cannula is in the expanded state when the impeller is in the deployed configuration.

A pump for pumping fluid at a desired location according to another embodiment hereof includes a cannula having a compact state for insertion to the desired location and an expanded state; an impeller positioned within the cannula and having a hub and a plurality of blades supported by the hub, each blade having a proximal end attached to the hub and a distal end, the impeller having a stored configuration and a deployed configuration; a drive mechanism for rotating the impeller in the deployed configuration; and a vane assembly positioned in the cannula and having a vane hub and a plurality of vanes supported by the vane hub, each vane having a proximal end attached to the vane hub and a distal end, the vane assembly having a stored configuration and a deployed configuration. The blades in the stored configuration of the impeller are compressed so as to move the distal ends of the blades towards the hub, and the blades in the deployed configuration of the impeller extend away from the hub. The vanes in the stored configuration of the vane assembly are compressed so as to move the distal ends of the vanes towards the vane hub, and the vanes in the deployed configuration of the vane assembly extend away from the vane hub. The vane assembly is connected to the impeller so that the vane assembly moves with the impeller in a longitudinal direction of the cannula and so that the vane assembly does not rotate with the impeller. The cannula is in the expanded state when the impeller and the vane assembly are in the deployed configuration.

A still further embodiment of a pump for pumping fluid at a desired location according to the present invention includes a cannula having an inlet end, an outlet end, a compact state for insertion to the desired location and an expanded state. The cannula includes a generally tubular reinforcing matrix, a layer of a first polymer at least partially coating an exterior of the reinforcing matrix and a layer of a second polymer different from the first polymer in a region adjacent the inlet end of the cannula. An impeller is positioned within the cannula and has a hub and a plurality of blades supported by the hub, each blade having a proximal end attached to the hub and a distal end, the impeller having a stored configuration and a deployed configuration. A drive mechanism is provided for rotating the impeller in the deployed configuration. The blades in the stored configuration of the impeller are compressed so as to move the distal ends of the blades towards the hub, and the blades in the deployed configuration of the impeller extend away from the hub. The cannula is in the expanded state when the impeller is in the deployed configuration.

A pump for pumping fluid at a desired location according to yet another embodiment hereof includes a cannula having an inlet end, an outlet end, a compact state for insertion to the desired location and an expanded state. The cannula includes a generally tubular reinforcing matrix having a plurality of circumferential rings each having an undulating pattern including a plurality of apexes pointing toward the inlet end and defining a plurality of recesses pointing toward the outlet end, and a plurality of apexes pointing toward the outlet end and defining a plurality of recesses pointing toward the inlet end. The matrix further includes a plurality of connectors, each connector connecting one of the apexes pointing toward the outlet end in one of the rings to an adjacent one of the rings. An impeller is positioned within the cannula and has a hub and a plurality of blades supported by the hub, each blade having a proximal end attached to the hub and a distal end, the impeller having a stored configuration and a deployed configuration. A drive mechanism is provided for rotating the impeller in the deployed configuration. The blades in the stored configuration of the impeller are compressed so as to move the distal ends of the blades towards the hub, and the blades in the deployed configuration of the impeller extend away from the hub. The cannula is in the expanded state when the impeller is in the deployed configuration.

Yet a further embodiment of a pump for pumping fluid according to the present invention includes a cannula having an inlet end, an outlet end, a compact state for insertion to the desired location and an expanded state. The cannula includes a generally tubular reinforcing matrix and a layer of a first polymer at least partially coating an exterior of the reinforcing matrix, the reinforcing matrix including a plurality of circumferential rings each having an undulating pattern including a plurality of apexes pointing toward the inlet end and defining a plurality of recesses pointing toward the outlet end, and a plurality of apexes pointing toward the outlet end and defining a plurality of recesses pointing toward the inlet end. At least one region of a second polymer different from the first polymer overlies the first polymer layer and connects one of the apexes pointing toward the outlet end in one of the rings to at least one other ring. An impeller is positioned within the cannula and has a hub and a plurality of blades supported by the hub, each blade having a proximal end attached to the hub and a distal end, the impeller having a stored configuration and a deployed configuration. A drive mechanism is provided for rotating the impeller in the deployed configuration. The blades in the stored configuration of the impeller are compressed so as to move the distal ends of the blades towards the hub, and the blades in the deployed configuration of the impeller extend away from the hub. The cannula is in the expanded state when the impeller is in the deployed configuration.

Yet another embodiment described herein is directed to a method of compressing a percutaneous blood pump. This method can include providing a percutaneous blood pump that can include a non-expandable retainer sheath and a cannula having an expandable portion. The expandable portion of the cannula can include one or more guidance aids. This method can subsequently include using the one or more guidance aids to advance a proximal portion of the expandable portion of the cannula into a distal portion of the retainer sheath.

Another embodiment described herein is directed to a method of collapsing an expandable pump. This method can be used, for example, for preparing a percutaneous blood pump for insertion into a patient. This method can include providing a percutaneous blood pump that can include an expandable distal portion having a proximal end, a distal end, a tubular matrix extending between the proximal and distal ends, an impeller disposed within the duct between the proximal and distal ends, and a sheath. In some embodiments, the sheath can have a generally non-expanding distal portion. For example, the sheath can be configured to have a substantially constant cross-section in the absence of a radially outwardly directed force. In some arrangements involving funnel-less deployment and retraction, there can be some deformation of the sheath while still achieving the benefits of minimizing potential pooling of blood. This method can also include providing relative motion between the distal portion of the sheath and the proximal end of expandable portion such that the distal portion of the retainer sheath applies a radially inward force to induce radial collapse of a distal region of the tubular matrix to facilitate collapse of the expandable portion into the sheath.

In one technique, collapse of a distal region is facilitated by providing a guidance aid coupled with the expandable portion, e.g., at or adjacent to a proximal end of the expandable portion to assist in the collapse of the expandable portion. The guidance aid can be any structure that locally stiffens a portion of the expandable portion of the duct (e.g., a proximal portion or axially extending regions, as discussed below). In one example, the guidance aid can be a connector associated with the expandable portion. In another example, the guidance aid can be a region of elastomeric material.

In another method for preparing a pump system, the system is provided with a lumen that can be selectively opened and closed to enable the guidewire to be received in the lumen. For example, the lumen can include a flow regulator that includes a blocking member and a surface that is adapted to mate with the blocking member, such that upon such mating the flow of a fluid is regulated (e.g., limited or completely prevented). In some embodiments, the blocking member and mating surface can be engaged to provide a seal against flow of fluids proximally in one more and/or distally in another mode within the lumen. The blocking member can be disengaged to permit the guidewire to pass through the flow regulator such that the guidewire is disposed both proximally and distally of, e.g., directly across, the flow regulator. In one embodiment, the flow regulator is disposed in a hub of the pump system and the flow regulator is disengaged by deforming the hub and displacing the blocking member into a deformed volume of the hub.

In another method for preparing a pump system, the system is provided with a duct and a device positioned within the duct for inducing axial flow of blood through the duct. The duct can be a flexible member. In one embodiment, the duct is expandable to enlarge the flow carrying capacity of the pump system. In one embodiment, the duct is collapsible to facilitate lower profile delivery, e.g., entry into a fluid system through a small aperture. The duct can be collapsible to a delivery configuration and expandable to an operating configuration. In some embodiments, the duct can be buttressed by one or more members that extend transversely to the flow direction in the duct. The member(s) have a transverse profile, which can be a radial length from an end adjacent to a central zone of the duct to an opposite end or which can be a circular circumference defined by the radial length between the ends of the members. In one embodiment, the members are configured as vanes that are rigid enough to substantially maintain the inner surface of the duct away from the flow inducing device, but are collapsible to facilitate crossing of the pump system through an aperture smaller than the transverse profile of the vanes. In one technique for preparing the pump for insertion through the small aperture, the buttressing members (e.g., vanes) are collapsed by a constraining structure, for example by circumferentially wrapping the members about a longitudinal axis of the duct and holding the members in the circumferentially collapsed state.

Further embodiments concern various methods of manufacturing the apparatus and pumps discussed above. Other embodiments are directed to methods of treating a patient, such as by performing one or more method steps within the body of a patient with the pumps and apparatuses described herein.

BRIEF DESCRIPTION OF THE DRAWINGS

A more complete appreciation of the subject matter of the inventions and the various advantages thereof can be realized by reference to the following detailed description, in which reference is made to the accompanying drawings in which:

FIG. 8A is a partial longitudinal cross sectional view of the blood pump of FIG. 1 in a deployed configuration;

FIG. 8B is a partial longitudinal cross sectional view of the blood pump of FIG. 1 in a retracted position;

DETAILED DESCRIPTION OF THE PREFERRED EMBODIMENT

I. Apparatus

Figure 1:
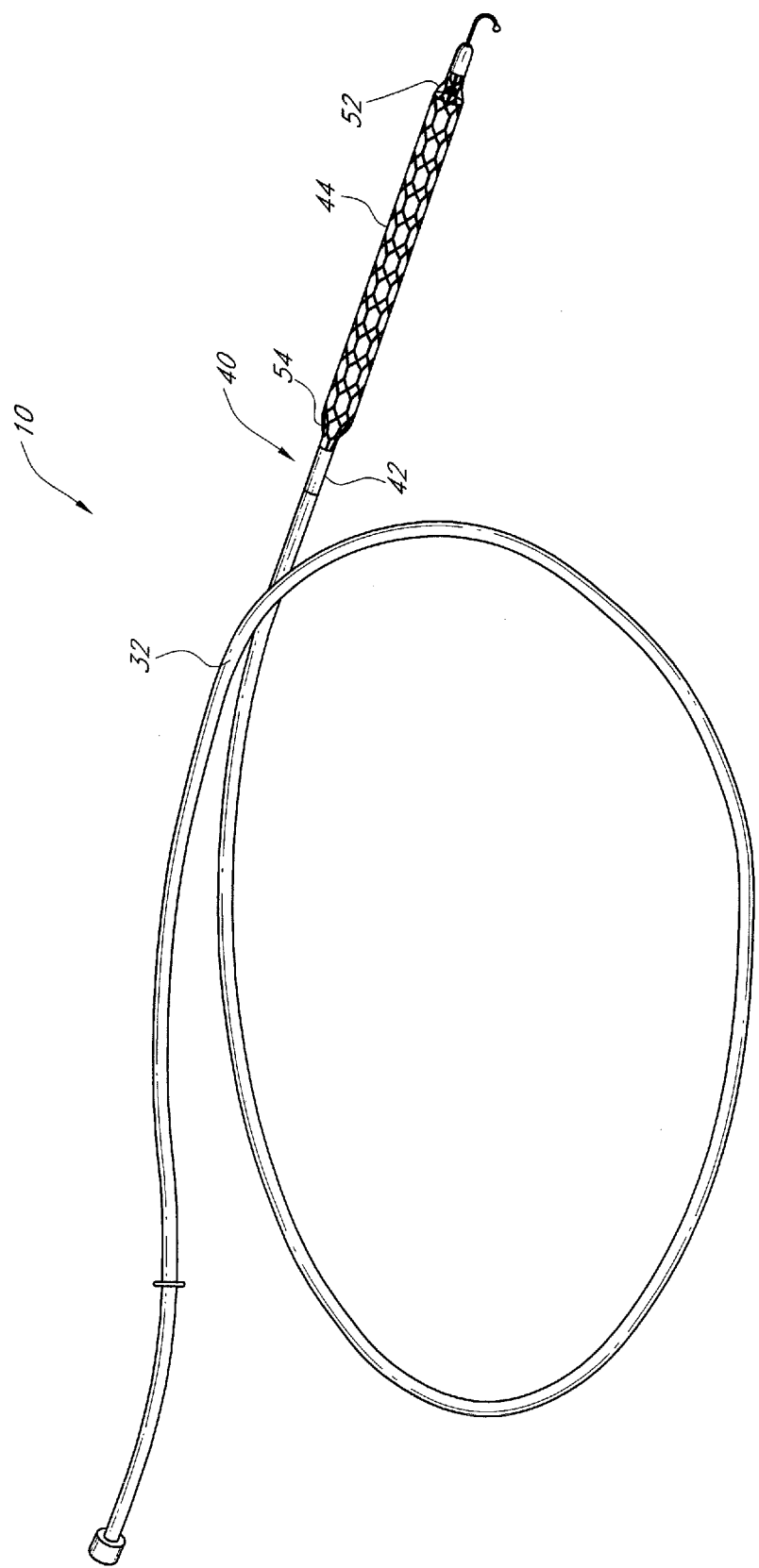
FIG. 1 is a perspective view of one embodiment of a blood pump according to the present invention.

A blood pump 10 according to the present invention has various applications within the human body, including as a left ventricle assist device, as a right ventricle assist device, for supplementing blood flow to organs, and the like. Referring to FIGS. 1 and 2A-C, blood pump 10 can include three main components, a rotatable impeller 20; a cannula 40 in which the impeller 20 resides; and a retainer sheath 60 overlying the cannula 40. Although each of these parts will be described generally below, blood pump 10 can include any or all of the structural arrangements and features described in co-pending U.S. application Ser. No. 11/728,051 the disclosure of which is hereby incorporated by reference herein.

A. Impeller

Impeller 20 includes a hub 22 and a plurality of blades 24. Blades 24 can be foldable against hub 22 so as to reduce the cross-sectional size of impeller 20 for percutaneous insertion into the body. Once impeller 20 has been located in a desired position, blades 24 can be expanded away from hub 22 using the stored potential energy of the folded blades so as to place impeller 20 in operation for pumping blood. A rotatable drive shaft 26 couples hub 22 to a motor (not shown) that can be located outside of the patient, thereby imparting a rotational drive to the impeller. Drive shaft 26 can have a substantially rigid portion 28 at its distal end which is connected to impeller 20 (see FIG. 8a), and a substantially flexible portion 30 (see FIG. 9). In some embodiments, the substantially flexible portion 30 extends along a majority of the length of the drive shaft 26. Advantageously, this flexibility can promote ease of the delivery of the pump 10 into a patient's anatomy. The flexible portion 30 can be formed from a metal or polymer braid which is easily bendable, or from a composite braid to reduce heating from friction as drive shaft 26 rotates. The flexible portion 30 of the drive shaft can be housed within a flexible tube 32 which supports the flexible portion and maintains its shape as it is driven rotationally. Advantageously, a flexible portion 30 formed from a composite braid can have a generally smooth outer surface, thus reducing friction between flexible portion 30 and flexible tube 32. The flexible tube 32 can be formed from a conventional flexible biocompatible tubing, including polymer tubing, coiled metal tubing and the like. In one embodiment, the flexible tube 32 is preferably formed from a polymer, such as polytetrafluorethylene. The proximal end of drive shaft 26 can be connected to the motor for rotating the drive shaft and impeller 20. Alternatively, drive shaft 26 can be omitted, and electric or fluid power for rotating impeller 20 can be provided through a rotor/stator assembly positioned proximally of the impeller (e.g., near the distal end of the blood pump 10, in the patient when deployed).

Drive shaft 26 and the hub 22 of impeller 20 can each be formed with an internal lumen 70 to allow a guide wire 72 to pass therethrough. Together, lumen 70 and guide wire 72 can assist in positioning blood pump 10 within the patient, though a guidewire may not be necessary in delivering or positioning the blood pump 10. Guide wire 72 may be wire wound and can have an outer diameter in the range of from about 0.305 mm (0.012 in) to about 0.889 mm (0.035 in) and in one embodiment can have a J tip 74 which facilitates navigation of the tortuous arterial pathway from a peripheral (e.g., the femoral) insertion site to the cardiac left ventricle chamber when used as a left heart assist device. Guide wire 72 can have one or more additional distal features, such as a spherical shape, or a valve plug 76 to plug a hole in impeller 20 (or other distal structure that is in fluid communication with the lumen 70) after withdrawal of the guide wire 72.

FIGS. 8A and 8B show that the rigid portion 28 of drive shaft 26 can be supported by one or more bearings 80 retained in a bearing housing 84. A saline solution can be directed into bearing housing 84 through internal lumen 70, and the bearing unit end seal 86 can be dimensioned so that a very small quantity of clean saline solution is infused into the patient (approximately 1-2 cc/hr). This fluid flow helps clean impeller 20 and dampens drive shaft vibrations. The fluid flow can also prevent blood from entering bearing housing 84 and compromising its operation and life. If the density of the rigid portion 28 of drive shaft 26 is approximately the same as that of the saline solution or other introduced fluid, most of the vibration can be damped. The rigid portion 28 of drive shaft 26 can be formed from carbon or other fiber and polymer composite which has a lower density than metal and more closely matches the density of the saline solution. Other lower density drive shafts and/or other higher density fluids can be used for vibration damping. The saline solution or other fluid can be introduced to bearing housing 84 through openings 88 in hollow drive shaft portion 28.

1. Check Valve Arrangements & Methods of Manufacture

Figure 10A:
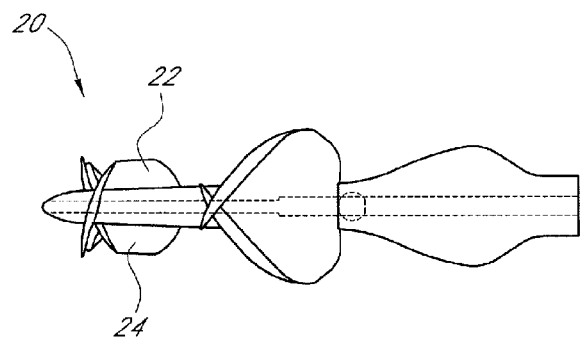
FIG. 10A is a schematic view of the impeller of FIG. 2A, further including a ball check valve.
Figure 10B:
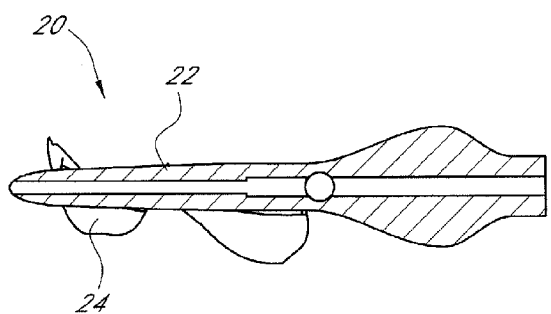
FIG. 10B is an enlarged partial cross sectional view of the impeller of FIG. 2A showing a manufacturing state of the ball check valve.
Figure 10C:
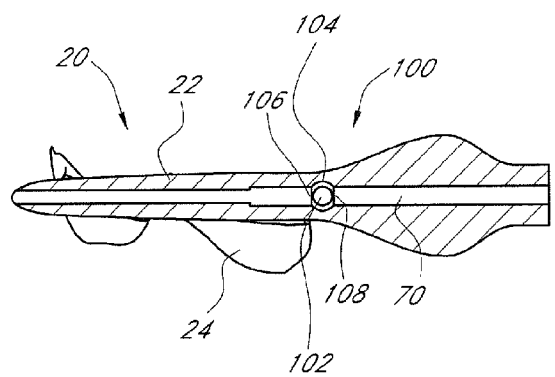
FIG. 10C is an enlarged partial cross sectional view of the impeller of FIG. 2A showing the ball check valve after manufacturing has been completed.

In a preferred arrangement, impeller 20 can be provided with a ball check valve 100, as shown in FIG. 10A, for preventing leakage of fluid through lumen 70. As shown in FIG. 10C, check valve 100 includes a spherical ball 102 having a first diameter, positioned within a spherical cavity 104 having a diameter which is greater than the first diameter so that ball 102 is freely movable within the cavity. Depending upon the fluid pressure differential in the lumen 70 of impeller 20, ball 102 will be pushed against a structure to prevent flow, such as a distal valve seat 106 or a proximal valve seat 108 between cavity 104 and lumen 70. That is, when the pressure of the saline flow distally or outwardly through lumen 70 is greater than the pressure of the blood flow proximally or inwardly through lumen 70, ball 102 will be pushed against distal valve seat 106 to prevent the flow of saline out through impeller 20. On the other hand, when the pressure of the blood flow inwardly through lumen 70 is greater than the pressure of the saline flow outwardly through lumen 70, ball 102 will be pushed against proximal valve seat 108 to prevent the flow of blood into the interior of drive shaft 26.

In order for check valve 100 to operate properly, ball 102 should have a density that is less than the density of the fluid (either blood or saline) within cavity 104 so that the ball is not thrown outwardly by centrifugal forces when impeller 20 is rotated. When formed with an appropriate density, ball 102 will self-center during impeller rotation and will be pushed against either valve seat 106 or valve seat 108 depending upon the pressure differential in cavity 104. Moreover, an appropriately designed check valve 100 will have little impact on the balance and stiffness of impeller 20.

Figure 10D:
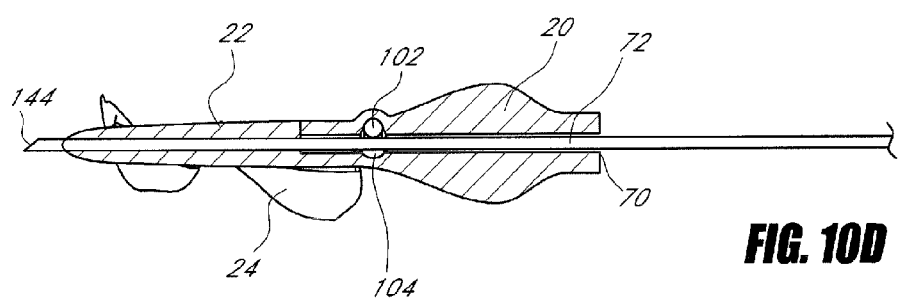
FIG. 10D is an enlarged partial cross sectional view showing a guide wire passing through the ball check valve of FIG. 10C.

Despite the presence of check valve 100 in the path of lumen 70, guide wire 72 is still able to pass through the lumen to enable blood pump 10 to be advanced over the guide wire 72 for placement at the desired location within the patient. In that regard, impeller 20 is preferably formed from a flexible, elastic material which can readily be deformed and which will return to its original shape once the deformation force has been removed. Thus, by forcing ball 102 to one side of lumen 70, such as through the use of a tapered pin or similar device, impeller hub 22 will deform, providing a clear path through lumen 70 for guide wire 72. In one embodiment, guide wire 72 can include a tapered and/or angled distal tip 144 which helps to push ball 102 to one side of the lumen 70, as shown in FIG. 10D. As a result of the deformation of hub 22, guide wire 72 is able to pass through check valve 100 with a minimum amount of friction so that blood pump 10 can be easily advanced over the guide wire 72. Once blood pump 10 is properly positioned and guide wire 72 is removed, hub 22 will return to its original shape and check valve 100 will operate normally.

One technique for forming check valve 100 is to coat ball 102 with a thin layer of a water soluble wax or similar material. The coated ball can then be supported in a mold, such as by attaching a pair of axially aligned rods having a small diameter to either side of the wax coated ball, and impeller 20 molded around it, forming the structure shown in FIG. 10B. After impeller 20 has been removed from the mold, the wax layer can be removed from ball 102 by flushing with water to release the ball for free movement within cavity 104.

B. Cannula

Figure 3:
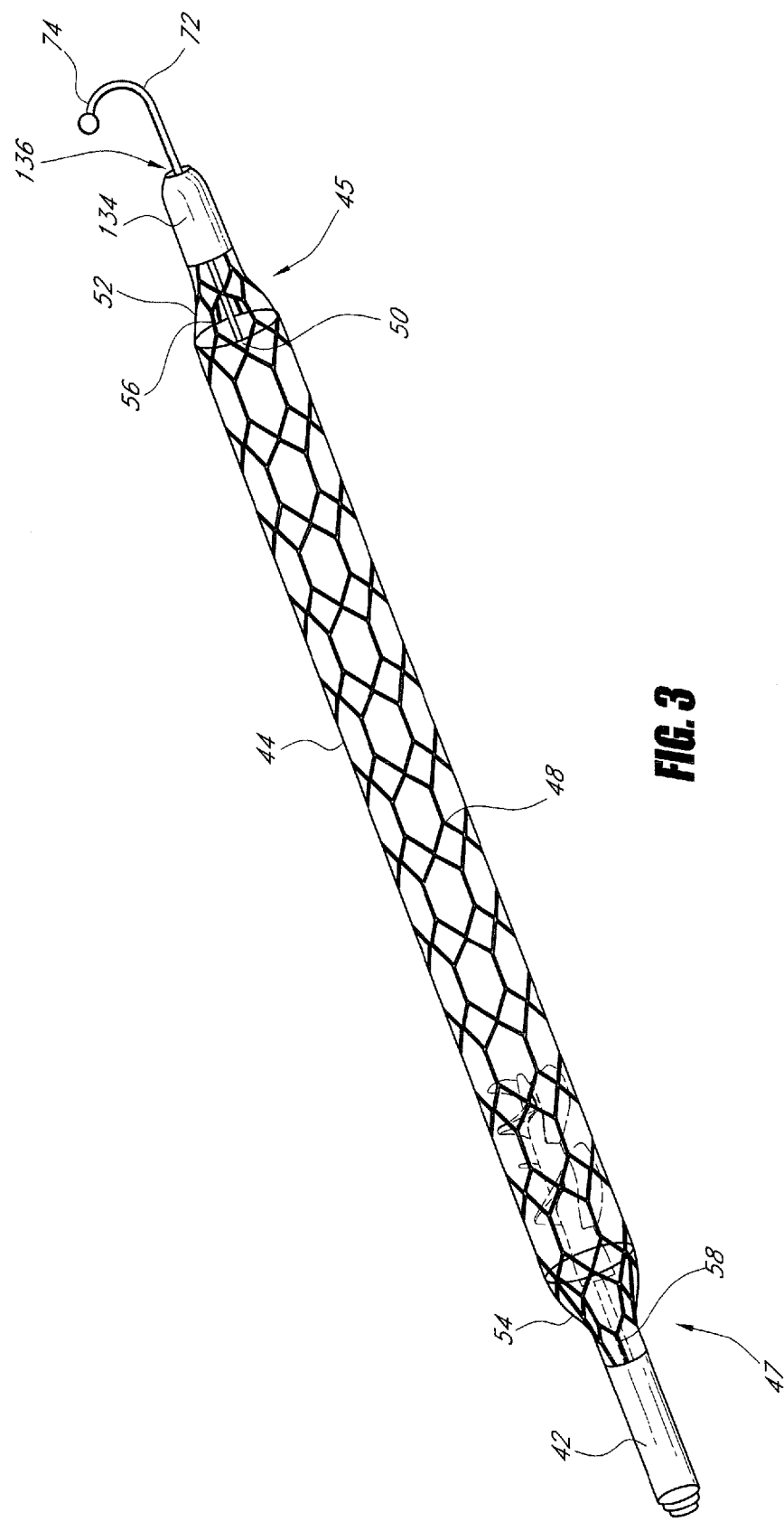
FIG. 3 is a perspective view of one embodiment of an expandable portion of the cannula shown in FIG. 1, the expandable portion being illustrated in the deployed state.
Figure 4:
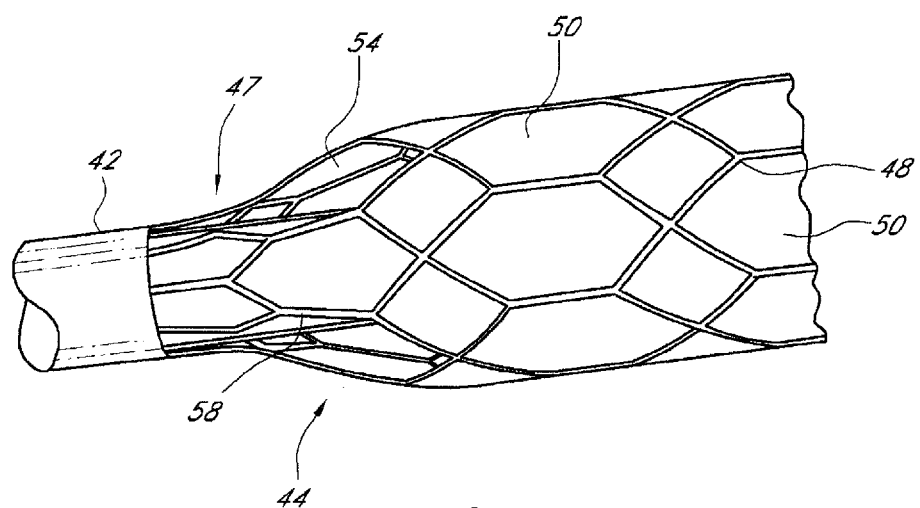
FIG. 4 is an enlarged perspective view of one embodiment of a discharge or proximal end of the expanded cannula having a hexagonal mesh.
Figure 5:
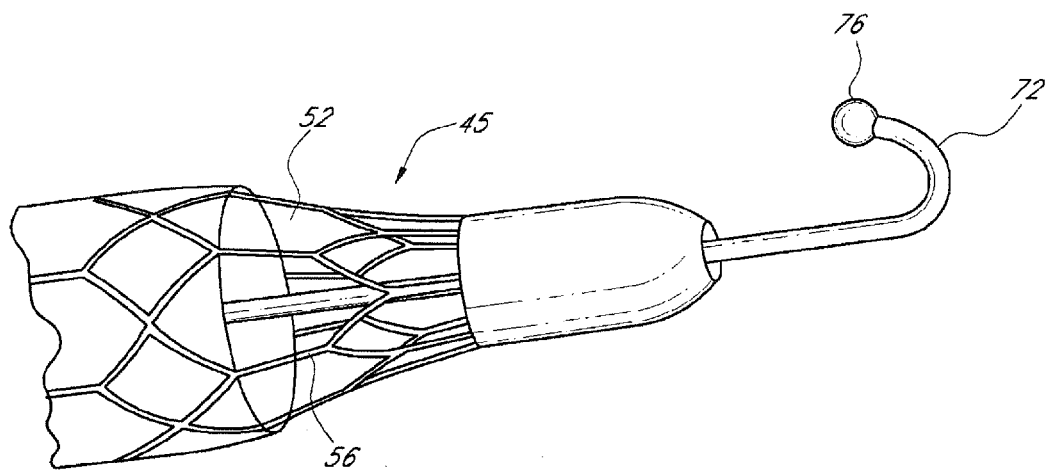
FIG. 5 is an enlarged perspective view of one embodiment of the inlet or distal end of the expanded cannula showing a guide wire disposed therein, the guidewire having a distal tip.
Figure 6A:
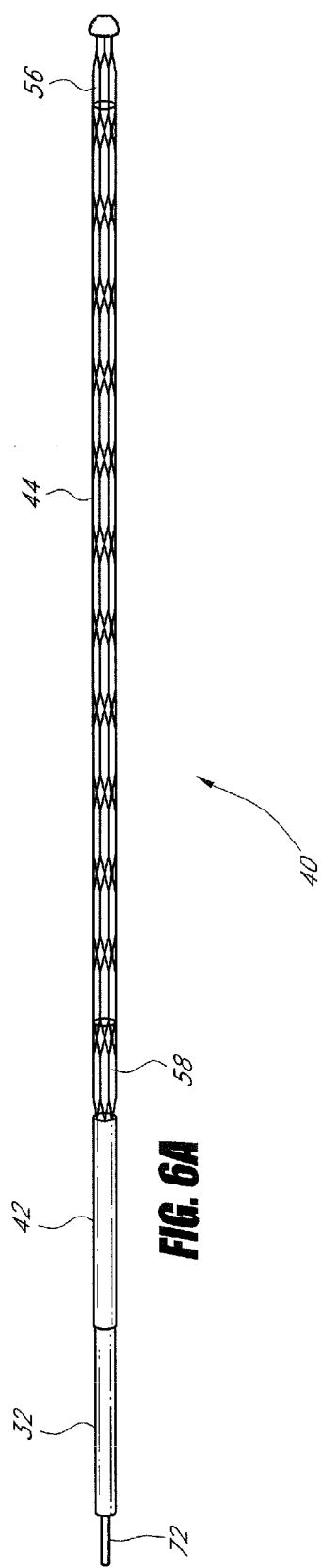
FIGS. 6A and 6B are side elevational views of the expandable portion of the cannula of the blood pump of FIG. 1 in stored and deployed configurations, respectively.
Figure 6B:
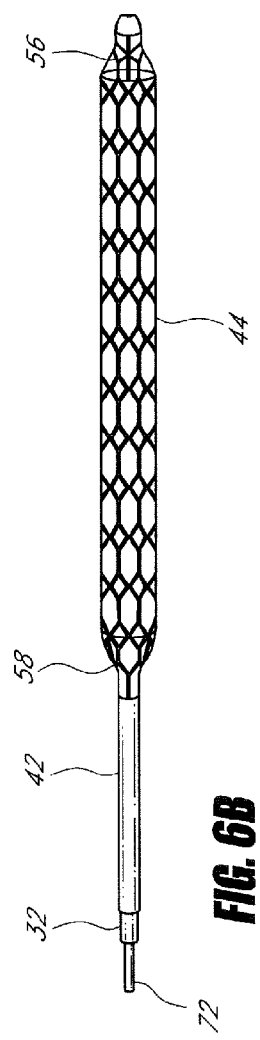

As shown in FIG. 3, cannula 40 has a non-expandable portion 42 at its proximal end and an expandable portion 44, in which impeller 20 resides, at its distal end. Preferably, expandable portion 44 is movable between a collapsed or stored configuration which retains blades 24 of the impeller in the folded condition, as shown in FIG. 6A, and an expanded or deployed configuration, as shown in FIG. 6B, which permits the blades to move away from hub 22 and into the use condition or operation state of the impeller 20. When used as part of a blood pump, expandable portion 44 in the deployed configuration can be in the range of from about 10 cm to about 50 cm long with a diameter in the range of from about 5 mm to about 15 mm. In the stored configuration, expandable portion 44 can have a diameter in the range of from about 2 mm to about 8 mm, allowing non-surgical insertion of blood pump 10 into a human subject through a superficial blood vessel, such as a femoral artery. The larger deployed diameter allows for higher fluid flow rates after insertion, and reduced friction pressure losses compared with a non-surgically inserted blood pump having a non expandable cannula.

Figure 9:
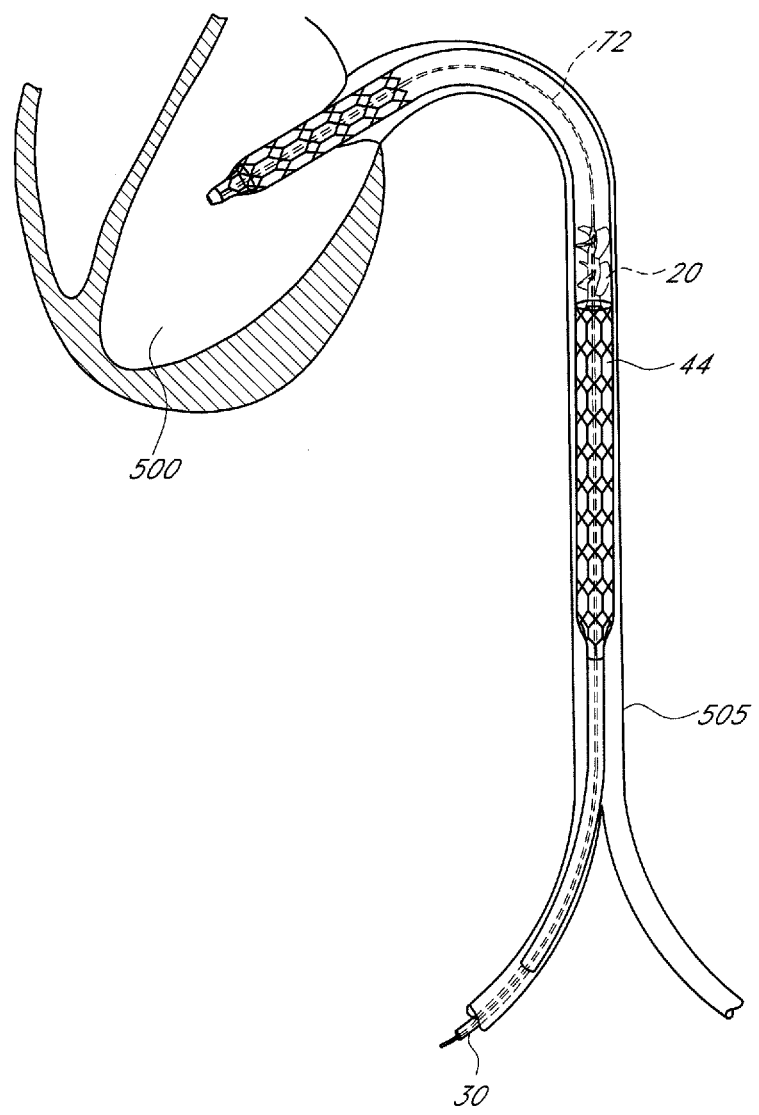
FIG. 9 is a highly schematic view showing the blood pump of FIG. 1 deployed in a patient.

The length of the expandable portion 44 can vary over a wide range. In some embodiments the expandable portion 44 can have a length from inlet 52 to outlet 54 that extends from a chamber of a patient's heart, such as a left ventricle 500, to a position proximal of the patient's aortic valve, such as the ascending aorta 505, as shown in FIG. 9. For example, expandable portion 44 can have a length in the range of from about 3 inches to about 4 inches. In other embodiments the expandable portion 44 can have a length from inlet 52 to outlet 54 that extends from a chamber of a patient's heart, such as a left ventricle 500, to a position in the patient's descending aorta. For example, expandable portion 44 can have a length in the range of from about 9 inches to about 11 inches.

1. Impeller Housings for Compressed and Deployed States

Optionally, cannula 40 can have a storage housing 46 for storing impeller 20 when the impeller 20 is in the stored state, as shown in FIGS. 8A-B. Storage housing 46 can be non-expandable. As described herein, storage housing 46 can move axially in a proximal direction to deploy the impeller 20, as shown in FIG. 8A, and can move axially in a distal direction to store the impeller 20, as shown in FIG. 8B. In other embodiments, the impeller 20 can be stored in the expandable portion 44 of cannula 40, which can expand for deployment of the impeller 20. In these embodiments, there may not be a difference in the relative axial use (e.g., deployed) location and the relative axial stored location of impeller 20.

The expandable portion 44 of cannula 40 can be formed from a mesh 48 having an elastomeric coating 50. As described below, mesh 48 predominantly defines the radial stiffness and bending characteristics of the expandable portion 44, while the elastomeric coating 50 enrobes the mesh to form a continuous duct having a fluid-carrying capability.

Figure 14A:
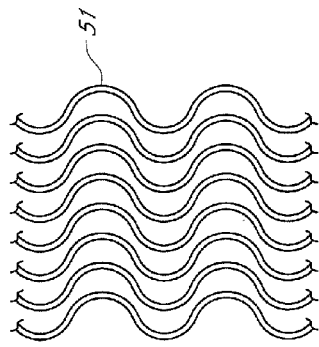
FIG. 14A shows highly schematic side views of different mesh designs.
Figure 14B:
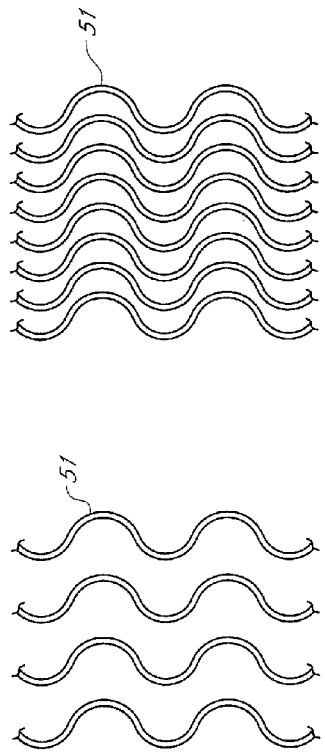
FIG. 14B shows a highly schematic side view of a mesh design.
Figure 14C:
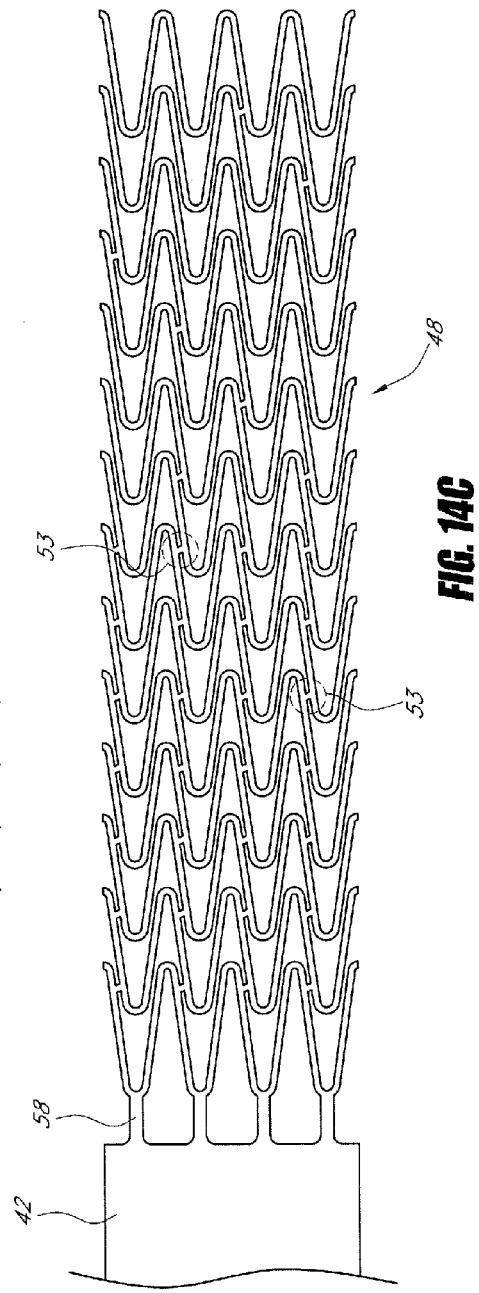
FIG. 14C depicts a material that can be incorporated into an expandable portion of a cannula and a main body.
Figure 15A:
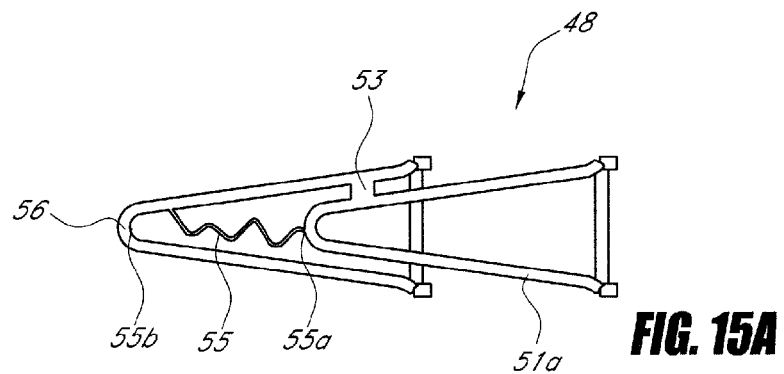
FIG. 15A shows a partial schematic view of a mesh design that includes a connector adjoining adjacent circumferential rings.
Figure 15B:
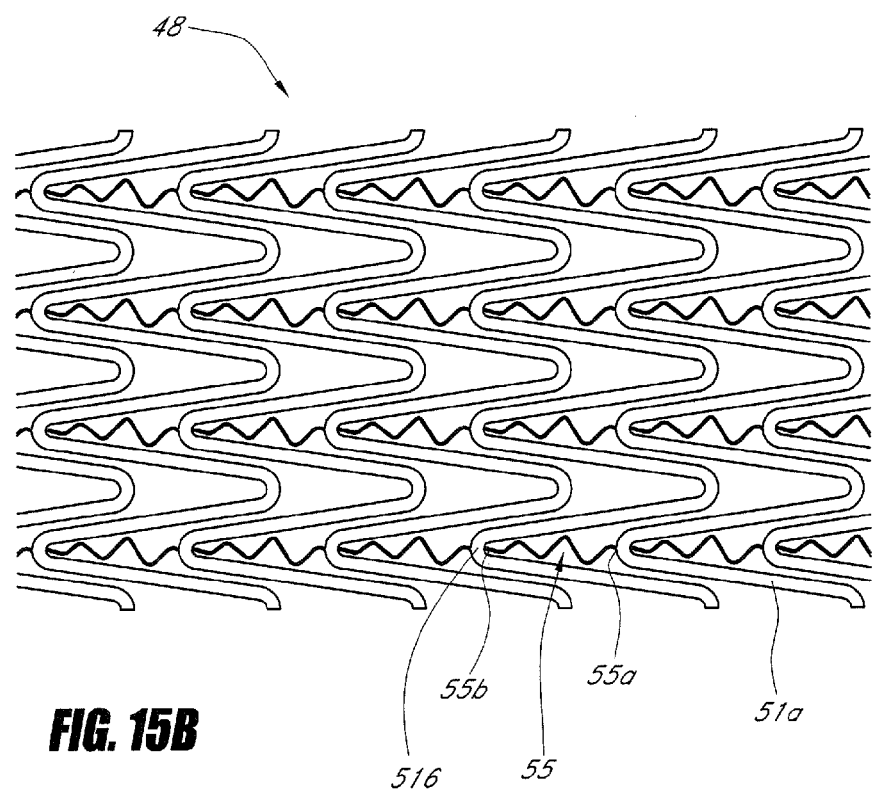
FIG. 15B shows a highly schematic side view of a mesh design useful to facilitate retraction of the expanded cannula into a sheath.

Mesh 48 can be formed from a flexible material, such as a polymer, metal, any shape memory material, or other material, and can include a machined cylinder with laser cut voids, a matrix of woven wires or filaments, or another configuration. The mesh can be in the form of a hexagonal cell matrix, or can include circumferential rings 51, as shown in FIGS. 14A-B. As depicted in FIG. 14C, mesh 48 can include a plurality of circumferential rings with axial connectors 53. Circumferential rings 51 predominantly control the radial characteristics, while axial connectors 53 affect axial stiffness and bending performance. Any other structures can be used for mesh 48 which are capable of moving between collapsed and expanded configurations and providing the cannula with sufficient strength and stiffness in the expanded configuration. As described further herein, mesh 48 can include one or more connectors 55, as shown in FIGS. 15A-B.

In some embodiments, the pattern of mesh 48 can be generally uniform throughout the expandable portion 44. In other embodiments, the pattern of mesh 48 can be generally non-uniform, such as by providing at least one region of enhanced or reduced mesh density in the expandable portion 44. Advantageously, an expandable portion 44 according to this embodiment can have varying structural characteristics along at least a portion of its length and/or circumference. It may be useful to stiffen the expandable portion 44 adjacent to the inlet 52 or outlet 54. This can be achieved by providing more connections between adjacent rings or by increasing the longitudinal density of the rings.

Although the non-expandable portion 42 of cannula 40 and mesh 48 can be formed from different materials, they preferably are formed from the same material. In one arrangement, mesh 48 can be formed from the same tube as forms non-expandable portion 42. In this regard, a memory metal alloy, such as nitinol, is a preferred material for forming both portions of cannula 40. In such arrangement, a constant diameter tube of the metal, having a metal thickness on the order of thousandths of an inch, for example, a thickness in the range of from about 0.005 inch to about 0.018 inch can be cut using a laser so as to leave a mesh structure adjacent one end. A constant diameter tube of the metal, having a metal thickness of between about 0.0018 inch and about 0.005 inch can be cut to leave a mesh structure adjacent one end in some embodiments. As shown in FIG. 14C, a material (e.g., a generally flat piece of metal) can be cut so as to leave a mesh 48 structure adjacent a first end and a non-expandable portion 42 adjacent a second end. Discharge struts 58 can connect mesh 48 to the non-expandable portion 42. The material can then be formed into a constant-diameter cylinder. The constant-diameter mesh 48 section can then be expanded/contracted radially to the desired shape using a mandrel, and optionally a clamping mechanism can be used to ensure the mesh conforms to the mandrel geometry. The material can be "shape set" to this configuration using, for example, heat treatment. Use of the laser-cutting and shape-setting steps enables complicated geometric patterns to be formed from the constant-diameter tube. The mesh diameter may be designed to be non-uniform to accommodate a certain anatomy or to achieve a certain hydrodynamic effect or for other reasons.

Figure 13A:
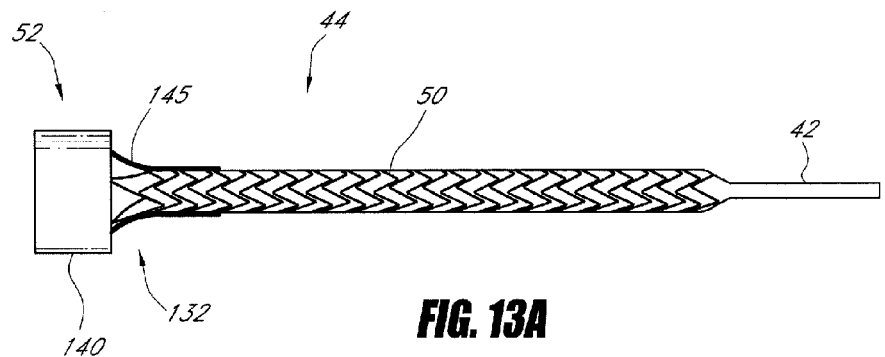
FIG. 13A is an enlarged, highly schematic elevational view showing a technique for stiffening an inlet end of an expandable portion of an expandable cannula.
Figure 13B:
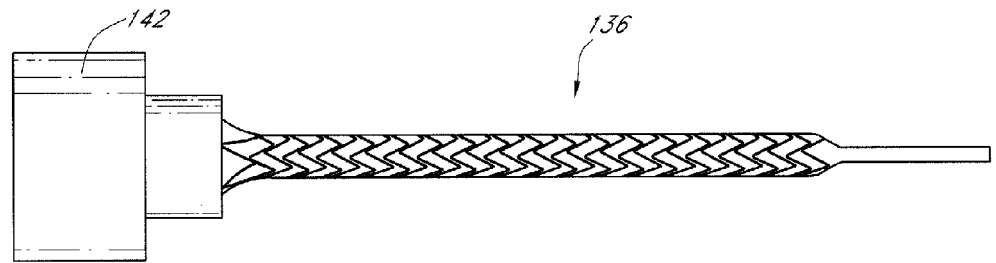
FIG. 13B depicts a mandrel that can be used when making a cannula having an expandable portion having one or more coatings.
Figure 13C:
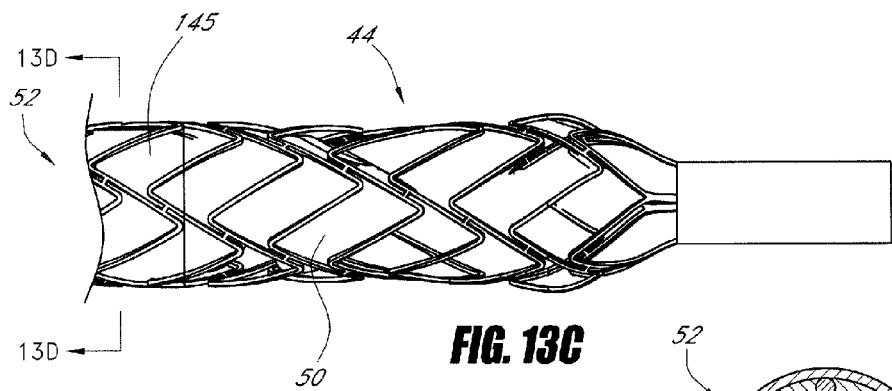
FIG. 13C shows an expandable portion of a cannula that includes a coated and stiffened inlet portion.
Figure 13D:
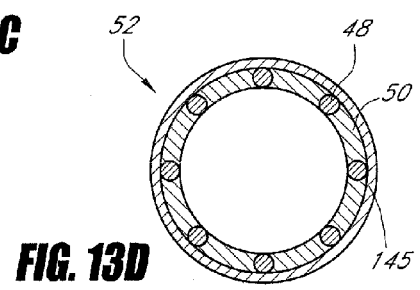
FIG. 13D is a schematic cross sectional view of the coated and stiffened inlet portion of FIG. 13C.

Once mesh 48 has been formed, elastomeric coating 50 can be applied to the inner and/or outer surface of the mesh. Coating 50 (which can be, for example, biocompatible, corrosion resistant and/or flow improving) can be formed by a solution casting method, by spray application over a mandrel or by other techniques known in the art, including forming the coating as a separate tube, fitting it over the mesh and heat shrinking it to produce a tight fit. An elastomeric polymer such as Elastane™ or Biospan™ can be used for coating 50, as can other polyurethanes and copolymers thereof, or other polymers. The thickness of coating 50 can vary over a wide range. As shown in FIG. 13D, the thickness of coating 50 can be generally equal to the thickness of mesh 48. In other embodiments, the thickness of coating 50 can be greater than the thickness of mesh 48. In some embodiments, the thickness of coating 50 can have a thickness in the range of from about equal to the thickness of mesh 48 to about twice the thickness of mesh 48. In other embodiments, mesh 48 can be embedded, encapsulated, or can have generally its entire surface area coated with coating 50. Mesh 48 and coating 50 together provide a flexible, expandable portion 44 of cannula 40 that is a conduit for fluid flow. Embedding or encapsulating mesh 48 in coating 50 can advantageously minimize sources of turbulence in the fluid flow path, and can reduce irritation to a blood vessel wall by providing a smooth outer surface. The expandable portion 44 of cannula 40 can be generally cylindrical with a flow inlet 52 at its distal end 45 and a flow outlet 54 at its proximal end 47. The portion between inlet 52 and outlet 54 is the expandable portion 44 of cannula 40. Mesh 48 can extend the entire distance from distal end 45 to proximal end 47, and/or from inlet 52 to outlet 54. Inlet 52 can include an outward taper or flare 132 (FIG. 13A) to aid in fluid flow into the expandable portion 44 of cannula 40. Taper 132 can be formed by the shaping of coating 50, or by the combined shaping of mesh 48 and coating 50.

Mesh 48 can be radially expandable in a way which imparts a minimal length change along the axial direction during radial expansion/contraction. The expandable portion 44 of cannula 40 can radially expand using stored potential energy, and thus is preferably a self-expanding device.

The radial stiffness of the expandable portion 44 can be controlled by controlling the thickness of mesh 48 and the geometric density of the mesh structure, which can vary along the length of cannula 40. Such variability is useful to match the cannula stiffness with the hydrodynamic loading imposed on blood pump 10, enabling a nearly constant radial deflection of the expandable portion 44 when operating as a flow duct (wherein the hydrodynamic pressure varies along the length). This is important in the region of the impeller 20 to provide a substantially constant operational gap between the tips of blades 24 and the inner diameter of portion 44 in the expanded condition.

Bending stiffness of the expandable portion 44 of cannula 40 is also a controllable parameter that can vary axially. For example, where circumferential rings 51 and axial connectors 53 are used to form mesh 48, the bending stiffness is predominantly controlled by the number and placement of the axial connectors 53, but also depends on the stiffness of the circumferential rings 51 and the stiffness of the elastomeric coating 50. The relative placement of the circumferential rings largely affects the radial stability of the expandable portion 44 during bending. For example, as shown in FIGS. 14A-C, mesh 48 can have a substantial amount of interleaving of adjacent circumferential rings 51. This configuration yields a very stable expandable portion 44 with respect to radial buckling caused by a bending deflection. Conversely, a mesh pattern with no interleaving yields an expandable portion 44 that can be prone to radial buckling during a bending deflection. Radial stiffness can be augmented via mesh thickness or mesh density. A dense mesh exhibits greater radial stability than a less dense mesh.

As shown in FIGS. 14A-C, circumferential rings 51 can be configured with an undulating or sinusoidal pattern with a plurality of apexes pointing toward the distal end 45 of expandable portion 44 of cannula 40 and defining a plurality of recesses pointing toward the proximal end 47 thereof, and a plurality of apexes pointing toward the proximal end 47 of expandable portion 44 and defining a plurality of recesses pointing toward the distal end 45 thereof.

FIG. 3 depicts expandable portion 44 of cannula 40 in the expanded state. Inlet 52 of the expandable portion 44 can be provided with a plurality of inlet struts 56 which prevent large debris from entering the expandable portion 44 to obstruct flow. Similarly, outlet 54 of the expandable portion 44 can be provided with a plurality of discharge struts 58 or vanes (not shown in this figure) which act as stator blades to remove swirl velocity from the flow discharged through outlet 54. Inlet struts 56 and discharge struts 58 can be part of mesh 48. Alternatively, discharge struts 58 can be formed with air foil type cross sections. Discharge struts 58 can connect the expandable portion 44 of cannula 40 to the non-expandable portion 42 or to storage housing 46. Preferably, non-expandable portion 42 discharge struts 58 and mesh 48 can be formed as a single, continuous structure from the same tube. In a variant hereof, discharge struts 58 and mesh 48 can be laser cut from one tube, and this portion can then be attached to non-expandable portion 42 by welding or other attachment techniques. Inlet struts 56 can also be formed from the same tube as mesh 48, discharge struts 58 and non-expandable portion 42.

2. Controlling Tip Gap

Figure 11:
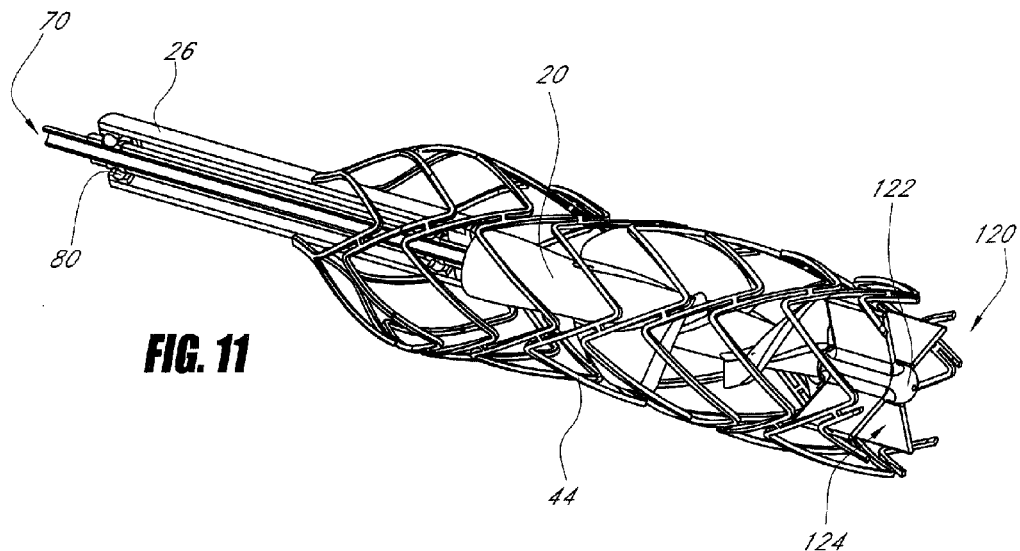
FIG. 11 is a perspective view of a blood pump in a deployed configuration, showing one embodiment of an inlet guide vane assembly.

The curvature of the aorta and the vascular geometry can cause the expandable portion 44 of cannula 40 to bend axially during operation. This bending can be such that the tips of blades 24 approach and retreat from the cannula walls with each rotation of impeller 20, impairing hydrodynamic functioning and, if the blade tips actually contact the cannula walls, causing hemolysis. Therefore, in order to keep impeller 20 substantially centered in the expandable portion 44 of cannula 40 during operation, blood pump 10 can be provided with a stator vane assembly 120, shown in FIG. 11, for preventing "cantilever" bending of the expandable portion about any one point to maintain consistent clearance between the impeller blade tips and the cannula wall. Stator vane assembly 120 can include a central hub 122 and a plurality of stator vanes 124 projecting radially outward therefrom. The stator vanes 124 can be made of an elastomeric material, such as those materials described herein as being suitable for impeller blades 24. Accordingly, stator vanes 124 can be foldable against hub 122 so as to not interfere with impeller 20 and expandable portion 44 achieving their fully collapsed condition. Moreover, stator vane assembly 120 preferably has about the same packing volume as impeller 20 so as to only minimally increase the forces required to collapse blood pump 10 and maintain it in the collapsed condition. Upon expansion of expandable portion 44 and impeller 20, stator vanes 124 will similarly expand. In their fully expanded condition, the free ends of the vanes 124 can contact the inner wall of expandable portion 44.

Figure 12:
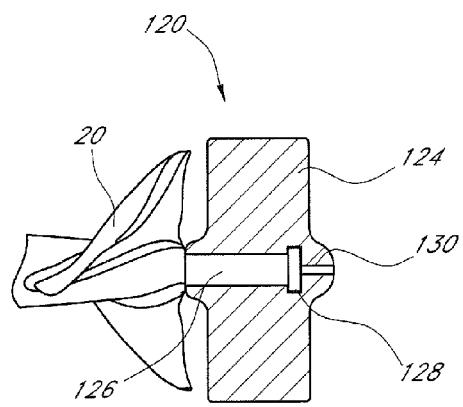
FIG. 12 is an enlarged partial side elevational view of the impeller and the inlet guide vane assembly of FIG. 11.

Referring to FIG. 12, stator vane assembly 120 can be mounted to the distal end of impeller hub 22 at an axial distance away from the impeller 20 so that it translates with impeller 20, but does not rotate with the impeller 20. In that regard, stator vane assembly 120 can include a hollow sleeve 126 in hub 122 coupled to a thrust bearing 128. Friction between the tips of stator vanes 124 and the coating 50 of expandable portion 44 will resist any torque transferred through thrust bearing 128 and thereby prevent the vanes from rotating within the cannula. A lumen 130 extends axially through hub 122 and communicates with lumen 70 in impeller 20 for slidably receiving guide wire 72.

In some embodiments, the lumen 130 is adapted to prevent fluid flow in at least one direction during at least one mode of operation. For example, the stator vane assembly 120 and/or the impeller 20 can be advanced along a guidewire extending through the lumen 130 prior to being activated to pump blood. In some embodiments, the guidewire will be removed before the pump is activated. In some cases, it is preferred that flow of blood into the lumen 130 is controlled or prevented, which can be accomplished by positioning a seal within the lumen 130. In some embodiments, the lumen 130 can be adapted for flexible self-sealing guidewire penetration. In another embodiment, a guide wire is not necessary for guiding the system, with the expandable portion 44 of cannula 40 in a collapsed state, to the target site due to inherent flexibility of the system and steerability in traversing the anatomy.

In some embodiments hereof, stator vanes 124 can be oriented at an angle to the direction of blood flow into inlet 52 of expandable portion 44 of cannula 40. Such orientation will induce a circumferential velocity component to the incoming blood, imparting a pre-swirl to the blood flow before it reaches impeller 20 so as to increase the net change in angular momentum of the fluid and thereby allow greater power extraction to the blood flow by the impeller 20.

In use, impeller 20 is positioned in the expandable portion 44 of cannula 40 such that stator vane assembly 120 is also positioned within the expandable portion 44. As expandable portion 44 deforms in the patient's vasculature, any forces exerted on the cannula will be transmitted through stator vanes 124 and hub 122 to impeller hub 22, thereby keeping impeller 20 substantially centered within expandable portion 44.

3. Variable Stiffness Flow Duct

The hydrodynamic performance of blood pump 10 can potentially be impaired by the flexibility of or damage to the expandable portion 44 of cannula 40 at inlet 52. That is, any flapping or other deformation of coating 50 at inlet 52 can result in a greater pressure drop for a given blood flow rate, and can also result in blood damage via hemolysis and/or thrombus formation. Accordingly, it is desirable to provide expandable portion 44 with a stiffened region at inlet 52 while maintaining the overall flexibility of the remainder of the expandable portion 44 both to accommodate the patient's vascular geometry and to facilitate the compressibility of the expandable portion 44 for percutaneous insertion.

In view of the foregoing, some embodiments can use two different polymers to form the coating 50 of expandable portion 44. As shown in FIG. 13A, the mesh 48 at the inlet end of expandable portion 44 can be masked with a wax, such as jeweler's wax 140 or some other high quality wax or other masking material to prevent this portion of the mesh from being coated with any polymeric material. A first elastomeric polymer such as Biospan™ or other flexible bio compatible polymer can then be solvent cast onto the entirety of expandable portion 44 to form coating 50. A second elastomeric polymer such as Hapflex™ 598 or another flexible bio compatible polymer can then be solvent cast to form a second coating 145 (e.g., generally in the shape of a ring) in the region adjacent inlet 52 and/or in any region where structural stiffness of coating 50 is desired. In some embodiments, the first elastomeric polymer is a relatively soft urethane and the second elastomeric polymer is a relatively stiff urethane. FIG. 13C depicts one embodiment of an expandable portion 44 having a stiffened region adjacent inlet 52. As shown in FIG. 13D, the stiffened region adjacent inlet 52 can include a first inner coating 50 and a second outer coating 145. The thickness of second coating 145 can vary over a wide range. As shown in FIG. 13D, the thickness of second coating 145 can be less than the thickness of first coating 50. In other embodiments, the thickness of second coating 145 can be greater than or generally equal to the thickness of first coating 50. In some embodiments, second coating 145 can have a thickness in the range of from about 0.5 times the thickness of first coating 50 to about 1.5 times the thickness of first coating 50. In some embodiments, the second coating 145 can at least partially coat the mesh 48. A mandrel 136 that can be used to coat expandable portion 44 in this manner is illustrated in FIG. 13B. In some embodiments, mandrel 136 can include a mounting structure 142, which can act as a base to support the mandrel 136.

4. Slideable Deployment of Impeller

Figure 7A:
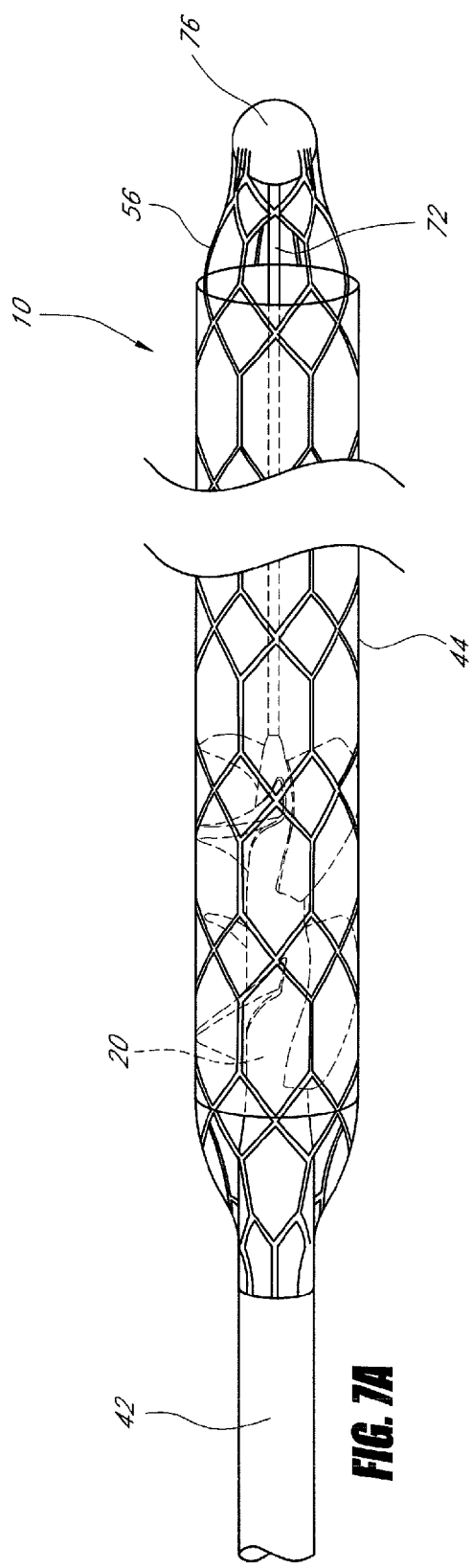
FIGS. 7A and 7B are longitudinal, highly schematic views of one embodiment of the blood pump of FIG. 1 in the deployed and stored configurations, respectively, showing system components.
Figure 7B:
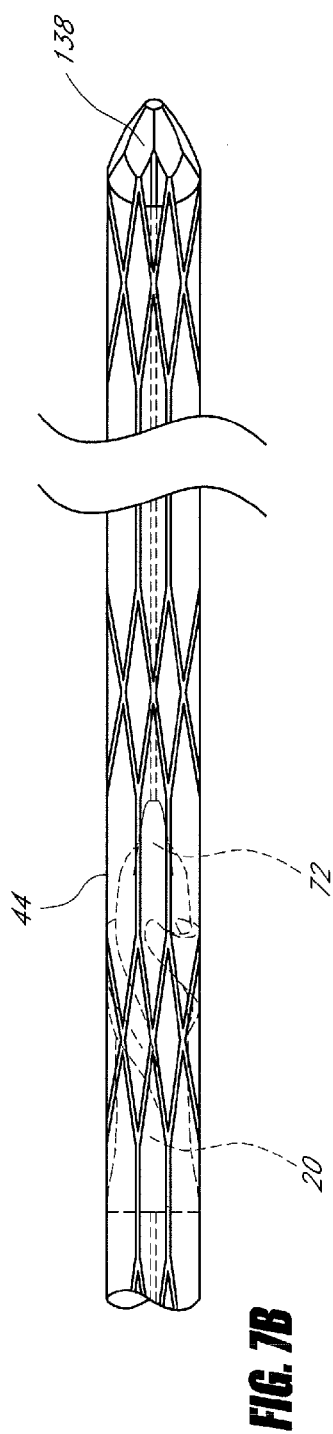

FIGS. 8A and 8B show an embodiment of blood pump 10 having an axially slidable storage housing 46. As can be seen in these figures, bearing housing 84 can have a reduced diameter portion 90 between its ends housing bearings 80. This reduced diameter portion thus defines a longitudinal space for sliding movement of an internal rib 94 defined by an indented annular channel 96 in storage housing 46. In use, after the expandable portion 44 of cannula 40 has been expanded (although not shown in FIGS. 8A-B, these structures would be to right of the structures shown, as illustrated in FIGS. 7A-7B), the impeller 20 can be released from a stored configuration to a deployed configuration by axially sliding the storage housing 46 in a proximal direction (e.g., away from the impeller 20). In the deployed condition shown in FIG. 8A, storage housing 46 has been moved proximally by the maximum extent permitted by the engagement of internal rib 94 with a proximal shoulder of bearing housing 84, thereby revealing blades 24 of impeller 20 for deployment. In the stored configuration shown in FIG. 8B, on the other hand, storage housing 46 has been moved distally (e.g., over and toward the impeller 20) to the maximum extent permitted by internal rib 94 contacting a distal shoulder of bearing housing 84. In this position, the distal end of storage housing 46 surrounds blades 24 of impeller 20, retaining them in the stored configuration.

In some embodiments, the use of storage housing 46, as shown in FIGS. 8A-B, allows for a greater degree of compaction of the pump 10. For example, in these embodiments, the impeller 20 and expandable portion 44 can be axially displaced relative to each other when in the collapsed or stored configuration in retainer sheath 60. In one arrangement, the impeller 20 is withdrawn to a position substantially entirely proximally of the expandable portion 44 and is collapsed within the storage housing 46. In this arrangement, the compaction of the expandable portion 44 is not limited by the presence of the impeller 20 within the portion 44. Accordingly, a pump 10 that includes storage housing 46 can have an expandable portion 44 with a diameter in the collapsed or stored configuration that is smaller than that of a pump 10 that does not include storage housing 46. Another benefit of the axial displacement of the structures that are compacted for delivery is that a device with a larger expanded size can be arranged with the same crossing profile as a device that does not provide for axial displacement but is smaller when expanded. For example, in embodiments that include storage housing 46, the expandable portion 44 advantageously can be configured to have a larger diameter in the deployed configuration as compared to embodiments that lack storage housing 46. An expandable portion 44 having a relatively larger diameter in the deployed configuration can be advantageous when a higher flow rate is desired.

C. Retainer Sheath and Retraction without Funnel

Figure 2A:
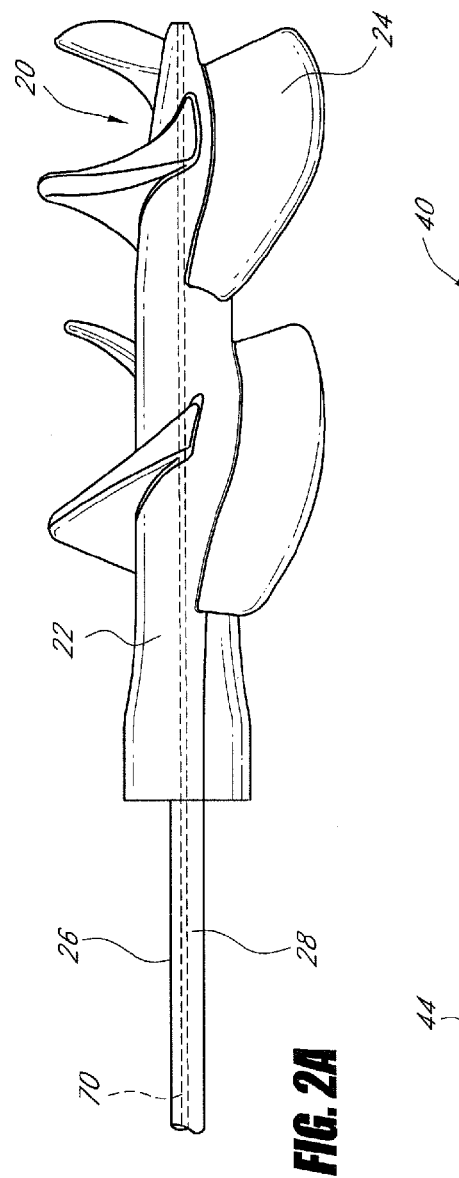
FIG. 2A is a side elevational view of one embodiment of the impeller portion of the blood pump of FIG. 1.
Figure 2B:
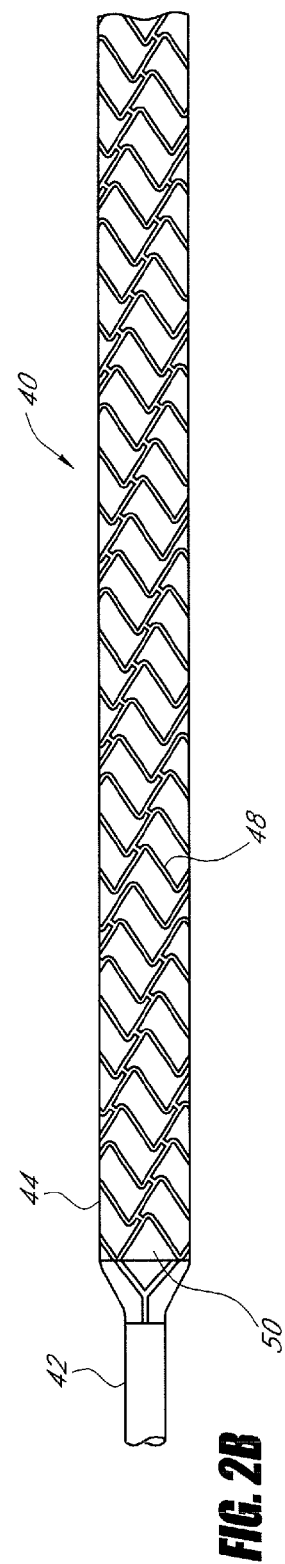
FIG. 2B is a partial side elevational view of one embodiment of a cannula in which the impeller of the blood pump of FIG. 1 operates.
Figure 2C:
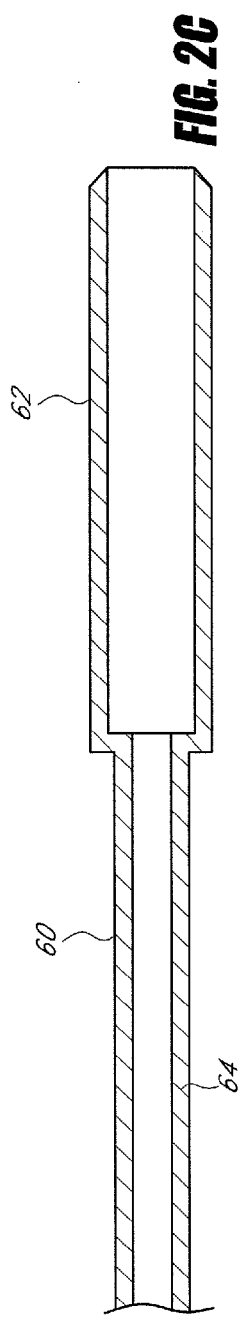
FIG. 2C is a partial longitudinal cross sectional view of one embodiment of an optional retainer sheath for use with the blood pump of FIG. 1.

Blood pump 10 can be inserted into the patient's body using a sheathless insertion procedure. Such procedure can employ a retainer sheath 60 having a distal portion 62 and a proximal portion 64, as shown in FIG. 2C. Distal portion 62 has an inner diameter and length which are sufficiently sized to receive the expandable portion 44 of cannula 40 and to hold the expandable portion, and with it impeller 20, in the collapsed condition during percutaneous insertion of blood pump 10 into and removal of blood pump 10 from a patient. The proximal portion 64 of retainer sheath 60 can serve as the housing for the flexible tubing 32, the flexible portion 30 of drive shaft 26 and/or for non-expandable portion 42 of cannula 40. Retainer sheath 60 is highly flexible, but has sufficient radial strength to resist collapsing or kinking as blood pump 10 is advanced to the desired deployment site. In a preferred embodiment, sheath 60 can be formed by a continuously coiled metal wire covered with a polymer tube or coating.

In some embodiments, retainer sheath 60 can be non-deformable, non-expandable, and/or can have a generally fixed-diameter. For example, retainer sheath 60 can be configured to not be distally expandable at any point during the compression of the expandable portion 44. In another example, retainer sheath 60 can be non-deformable, non-expandable, and/or can have a generally fixed-diameter when the expandable portion 44 is in its deployed configuration. In some embodiments, retainer sheath 60 can be distally deformable (e.g., expandable) when subject to a load.

The drive motor rotates drive shaft 26 without rotating cannula 40 or retainer sheath 60. The operation of blood pump 10 can be controlled and monitored by a control unit (not shown) which displays status and controls various functions. Sensors, such as a pressure sensor and flow rate sensor, can be affixed to various regions of the patient and/or to one or more locations on the blood pump 10.

As described herein, when the device is to be removed from a patient, the expandable portion 44 of the cannula 40 can be pulled into the retainer sheath 60. One or more guidance aids can be used to direct the expandable portion 44 into the retainer sheath 60. Advantageously, the use of a guidance aid, described further herein, can allow the expandable portion 44 to be collapsed or compressed without the use of an outward flare or funnel on the sheath. Mesh 48 of expandable portion 44 can include a guidance aid that can be designed to facilitate the retraction of the expandable portion 44 into a low profile distal portion of the retainer sheath 60.

Referring to FIG. 15A-B, one embodiment of the guidance aid includes a connector 55 joining adjacent circumferential rings 51 of mesh 48. A connector 55 can join a first ring 51a to an adjacent second ring 51b at a variety of different locations relative to the first and second rings 51a, 51b. In one embodiment, a connector 55 can connect the outer apex of a first ring 51a to a point on the second ring 51b such as the inner apex of the second ring 51b or on a point along a side of the second ring 51b. As shown in FIG. 15A, the first end 55a of connector 55 can be joined to the outside apex of a first circumferential ring 51a, while the second end 55b of connector 55 can be joined to a point along a side of the second circumferential ring 51b.

In another embodiment, the end 55a of connector 55 can be joined to the outside apex of one circumferential ring 51a, while the end 55b of connector 55 can be joined to the inside apex of the adjacent circumferential ring 51b, as shown in FIG. 15B. Connectors 55 can have a serpentine or flat coiled shape in order to maintain the flexibility of expandable portion 44. The connections of connector ends 55a to the outside apexes of rings 51 prevent the apexes from catching on or interfering with the end of retainer sheath 60 as expandable portion 44 is withdrawn into the retainer sheath by constraining the apexes and inhibiting expansion of an individual ring 51. As shown in FIG. 15B, connector 55 can be connected to a circumferential ring 51a, 51b only at end 55a or 55b, but at no other points in between.

Advantageously, the choice of connection point for first end 55a and second end 55b can affect the bending and radial stiffness characteristics of mesh 48 used for expandable portion 44. For example, an apex-apex connection (e.g., where first end 55a is joined to an apex of a first circumferential ring 51a and second end 55b is joined to an apex of a second circumferential ring 51b) generally yield mesh 48 with more bending flexibility than an apex-side wall connection (e.g., where one of first and second ends 55a, 55b is joined to an apex of a circumferential ring 51a, 51b and the other of first and second ends 55a, 55b is joined to a point along a side of a circumferential ring 51a, 51b). For example, this arrangement provides a greater distance between the points of connection such that a longer structure can be provided therebetween. This can enable the use of a more flexible structure, such as a slender spring-like connector 55, as shown in FIG. 15B.

However, the radial stiffness of an expandable portion 44 formed from mesh 48 having apex-apex connectors 55 can be less than the radial stiffness of an expandable portion 44 formed from mesh 48 having apex-side wall connectors 55. Those of ordinary skill in the art may appreciate that the width of a circumferential ring 51 can increase at the apex with the addition of connectors 55, thereby producing higher strains for a given deformation. Apex-apex connectors 55 can therefore be thinner than apex-side wall connectors 55 so as to avoid plastic strains that may result from connections on both the inside and outside radii of the apex. As a result, the radial stiffness of expandable portion 44 is generally reduced when apex-apex connectors 55 are used in forming mesh 48, as compared to apex-side wall connectors 55.

As shown in FIG. 15A, mesh 48 used to form expandable portion 44 can include a connector 55 and an axial connector 53. Advantageously, axial connector 53 can contribute to the axial stiffness of expandable portion 44 while connector 55 can contribute to the radial stiffness of expandable portion 44.

To retract expandable portion 44 into retainer sheath 60, an axial force in the proximal direction can be exerted on a member connected to the expandable portion 44 thus retracting the expandable portion 44 into the retainer sheath 60. This axial force can be advantageously transmitted through each circumferential ring 51 via the connectors 55 to pull the expandable portion 44 into the sheath 60. Furthermore, the relative location of connector ends 55a, 55b with respect to each circumferential ring 51a, 51b can facilitate a compact and orderly retraction of expandable portion 44. For example, in a configuration as shown in FIG. 15B where the connector ends 55a, 55b are attached to the outside apex of one circumferential ring 51a and the inside apex of a second circumferential ring 51b, respectively, the connectors 55 can guide the apexes to nest upon retraction, which can result in a stored configuration where the expandable portion 44 is relatively compact, as opposed to a configuration where the apexes are not nested upon retraction.

Figure 16:
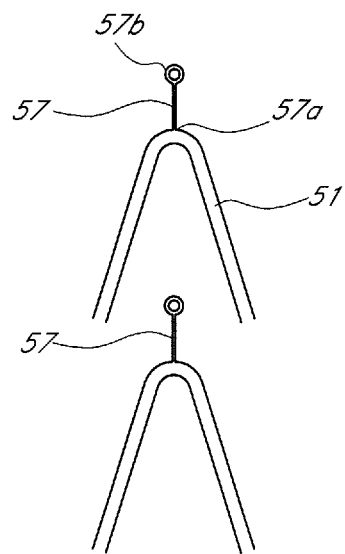
FIG. 16 shows a highly schematic view of an alternate embodiment of a mesh design useful to facilitate retraction of the expanded cannula into a sheath.

An alternate embodiment of mesh 48 which is also designed to facilitate the retraction of expandable portion 44 into retainer sheath 60 is shown in FIG. 16. In accordance with this embodiment, adjacent rings 51 of mesh 48 are not connected to one another. Rather, each of the outer apexes of a ring 51 is connected to one end 57a of a connector 57. The other end 57b of the connector 57 is not connected to the adjacent ring 51, but rather remains unconnected. Connectors 57 are designed to be sufficiently soft that the elastomeric coating 50 is able to guide the free ends 57b into retainer sheath 60 as expandable portion 44 is retracted, while the connectors 57 themselves act as guidance aids to guide the circumferential rings 51 into the retainer sheath. Connectors 57 can either be integrated into the design of mesh 48 or manufactured as separate pieces, possibly from a different material, and permanently attached to the mesh structure. As shown in FIG. 16, end 57b of connector 57 can be configured in the shape of an eyelet. Advantageously, the eyelet can enable a mechanical bond between coating 50 and connectors 57. In one arrangement, a mechanical bond is provided through the eyelet, e.g., by a process that causes the coating 50 to flow into and bridge the space through the aperture. Structures other than eyelets, such as recesses or depressions in the mesh 48 could be used to provide a mechanical bond structure with the coating 50. Alternatively, the coating 50 could have a recess for receiving the mesh 48, e.g., a depression having the same shape as the mesh 48, to provide a mechanical engagement therebetween. This mechanical bond can be stronger than the surface adhesion bond that would otherwise be present between coating 50 and connector 57 in the absence of the eyelet.

Figure 17:
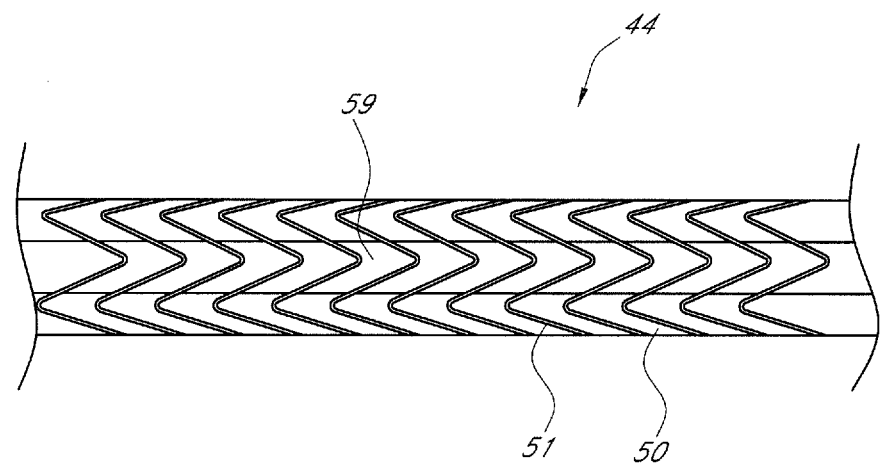
FIG. 17 shows a design of the expanded cannula useful to facilitate retraction into a sheath.

In combination with or as an alternative to designing mesh 48 to facilitate the retraction of the expandable portion 44 of cannula 40 into retainer sheath 60 without the use of a flare or funnel on the sheath, the coating 50 can be altered to facilitate such retraction. Thus, as shown in FIG. 17, some embodiments include a coating- or polymer-based guidance aid. Referring to FIG. 17, mesh 48 is made from a plurality of rings 51 that are not joined to one another by any directly attached connectors. Rather, coating 50 includes regions 59 of additional elastomeric material, of the same or different composition and physical characteristics as those of coating 50, applied to select areas. The regions 59 of additional elastomeric material can add an additional degree of stiffness to expandable portion 44. The overall flexibility of expandable portion 44 also depends on the geometry and physical characteristics of the additional regions 59.

The additional elastomeric material in regions 59 can be applied using the same solvent casting technique described above in connection with the formation of polymer ring 145 adjacent inlet 52. Alternatively, regions 59 can be formed separately and jointed to coating 50 in the desired locations. Regions 59 can extend either fully or intermittently along the length of expandable portion 44 of cannula 40 from proximal end 47 to distal end 45, and can have a variable geometry (e.g., length, width, and/or thickness) and variable properties (e.g., elasticity) along the length of expandable portion 44 to control the cannula properties.

In some embodiments, regions 59 can be generally elongate or rib-shaped between the proximal and distal ends of expandable portion 44. Regions 59 can also have a width sufficient to cover the apexes of rings 51. As shown in FIG. 17, additional material regions 59 can be applied in one or more sections along the length of expandable portion 44 in an area overlying the apexes of rings 51 and act as guidance aids by guiding the rings into retainer sheath 60 during retraction of the expandable portion 44 without the need for a funnel or flare at the end of the retainer sheath. For example, in one embodiment, region 59 is present at the proximal end of expandable portion 44. Advantageously, in this embodiment, region 59 is configured to guide the proximal end of expandable portion 44 into the retainer sheath. In another embodiment, region 59 is present on a section of expandable portion 44 overlying the impeller 20. In this embodiment, region 59 can advantageously provide additional strength to expandable portion 44 to aid in compressing the impeller 20. This embodiment can also advantageously minimize bulging or other uneven expansion of expandable portion 44 that may be caused by impeller 20.

As described herein, in some embodiments the design of mesh 48 can be non-uniform throughout at least a portion of the expandable portion 44. Those of ordinary skill in the art may appreciate that, as an alternative to or in combination with the regions 59, the non-uniform design of mesh 48 can similarly provide variable geometry and/or properties to the expandable portion 44.

II. Method

The apparatuses described herein can be used in various methods that can be performed to treat a patient or to prepare an apparatus prior to any treatment of a patient.

In some of the embodiments discussed above, systems are provided that enable percutaneous application of heart assist devices that can operate at high flow rates. In particular, certain components are configured to be actuated between an enlarged operating configuration and a collapsed configuration for transluminal delivery and/or withdrawal of the system.

A. Collapsing the System

As discussed herein in connection with FIGS. 6A-8B in connection with the pump 10, the expandable portion 44 of cannula 40 and the impeller 20 positioned therein can be actuated from an operational state to a collapsed state prior to insertion a patient.

In one technique, relative movement is provided between the impeller 20 and the housing 46 such that a proximal end of the hub 22 is moved into the housing 46. As the hub 22 is moved into the housing 46, a proximal edge of a proximal blade 24 is brought into contact with a distal edge of the housing 46, as shown in FIG. 8B. Further relative movement of the blade 24 causes the blade 24 to move from the deployed configuration to the stored configuration, as discussed above. In another technique, the impeller can be stored by moving housing 46 distally over impeller 20 to compress the blades 24.

To further collapse the pump 10, at least the expandable portion 44 of the cannula 40 can be compressed into a low profile state suitable for delivery. In one technique, the expandable portion 44 is configured to be collapsed without any distally expanding, e.g., funnel-shaped, devices being required. An example of the cannula 40 in a compressed state is shown in FIG. 6A.

In one technique, a distal portion of the retainer sheath 60 is advanced over a proximal end of the cannula 40 and is advanced over the non-expandable portion 42 to a location proximate to the expandable portion 44. As discussed above, the retainer sheath 60 preferably has sufficient radial strength to maintain its shape upon engagement with the expandable portion 44. This radial rigidity results in expandable portion 44 being compressed upon relative movement of the distal end of the retainer sheath 60 and the proximal end of the expandable portion 44 toward each other. In some embodiments, a compression tool is used to insert the expandable portion 44 of cannula 40 into the retainer sheath 60.

In one embodiment, the compression tool has a tapered internal diameter portion, such as an internal funnel or cone. This tapered internal diameter portion has a first end with a large diameter and a second end with a small diameter. In some embodiments the largest diameter of the tapered internal diameter portion can be generally equal to or larger than the outer diameter of expandable portion 44 of cannula 40 in its expanded configuration. In other embodiments the smallest diameter of the tapered internal diameter portion can be generally equal to or smaller than the inner diameter of the distal end of retainer sheath 60. The compression tool can have a unitary construction, or it can be made of two or more parts that form the internal tapered shape upon assembly. In use, the compression tool can be placed over or immediately adjacent to the distal portion of the retainer sheath 60 to aid in retraction of the expandable portion 44 into the retainer sheath 60. Advantageously, a compression tool made of two or more pieces can be more easily removable from the retainer sheath 60.

As discussed above, the expandable portion 44 of cannula 40 is structured to have sufficient radial strength in the expanded state to convey fluids between the inlet and outlet and to maintain a volume for movement of the impeller 20. The expandable portion 44 also is configured to respond to an axially and distally applied force on an outside surface of the expandable portion 44 to become radially compressed. In one arrangement, the connector 55, 57 is generally axially aligned. The connector 55, 57 can be configured such that a force applied to a proximal end of the connector 55, 57 is transferred through the connector to a distal end of the connector. This force is then applied to a circumferential ring 51 coupled with a distal end of the connector 55, 57 to cause the ring 51 to be urged radially inwardly toward a compressed state.

In another arrangement, the expandable portion 44 is stiffened by providing axially extending ribs that extend between a proximal end 47 and a distal end 45 of the expandable portion. The proximal and distal ends 47, 45 can be generally aligned with the direction of movement of the retainer sheath 60 relative to the expandable portion 44. For example, in one arrangement, the expandable portion 44 includes a plurality of circumferential rings separated from each other by spaces but coupled together by a flexible material forming a duct, as discussed above. The circumferential rings 51 can be embedded or enrobed in a polymer sleeve or film, as discussed above. Another region of material 59 can be provided on the expandable portion 44 that is adapted to cause radial compression of a portion of the expandable portion 44 that is disposed distal of the distal end of the retainer sheath 60. For example, the second region 59 can be made rigid enough, such as by having sufficient thickness, to act as a rib or beam. The rigidity of the second region 59 can be such that the relative movement of the distal end of the sheath 60 over the proximal end of the expandable portion 44 causes a force applied to the proximal end of the rib to collapse a length of the expandable portion 44 distal of the sheath 60. For example, the force applied by the distal end of the sheath 60 to the expandable portion 44 can be transferred along the rib by virtue of the stiffness of the rib to apply a force to a circumferential ring located distal of the distal end of the sheath 60.

The second region 59 also enables the expandable portion 44 to be guided into the distal portion of the sheath 60, which in some embodiments is fixed in shape, e.g., not distally expanded at any point during the compression of the expandable portion 44. As the expandable portion 44 is moved farther proximally relative to the sheath 60, the distal portion of the expandable portion 44 is compressed.

By configuring the expandable portion 44 to be collapsed without requiring a funnel or other distally enlarged structure, the overall profile of the pump 10 can be reduced. These and other methods for collapsing the expandable portion 44 can be performed prior to any application of the device to a patient.

As discussed above, the pump 10 can include a vane assembly 120 having vanes 124 that provide structural integrity to the impeller 20 and expandable portion 44 when they are deployed. The vanes 124 can be collapsed by any suitable technique, such as those described herein with respect to the collapse of impeller blades 24. For example, the vanes 124 can be collapsed by urging the vane assembly 120 proximally into storage housing 46. In yet another technique, the pump 10 can be compressed prior to insertion into the body by collapsing the expandable portion 44 of cannula 40 from the proximal end 47 toward the distal end 45, such as by advancement of the sheath 60 over the expandable portion 44. In this technique, as the expandable portion 44 is collapsed, a constraining force exerted on the expandable portion 44, e.g., by the sheath 60, can be transmitted to the vane assembly 120, causing the vanes 124 to bend and compress inward towards (e.g., wrap around) hub 122. For example, each vane 124 can have a hinge or a portion at which stress is concentrated adjacent its point of attachment to the hub 122, enabling the vane 124 to be compress circumferentially around the hub 122. For example, a portion of the vane 124 near the hub 122 can have a reduced cross-sectional area to enhance stress at that location. The stress can be enhanced to cause a strain in the vane 124 that is sufficient to move a distal portion of the vane to a low profile configuration upon collapse of the expandable portion 44. Other features that facilitate bending and compressing of the impeller blades 24 can also be applied to the vane assembly 120 to facilitate bending and compressing of the vanes 124.

B. Implanting the System

Once the expandable components at the distal end of the pump 10 are compressed, the pump can be delivered to a treatment site. In one technique, the expandable portion 44 of cannula 40 and the retainer sheath 60 disposed over the cannula 40 are percutaneously inserted into a patient's vasculature. Any suitable percutaneous insertion technique can be used, such as puncture of the skin and vascular access via the Seldinger technique.

In one technique, the expandable portion 44 and the retainer sheath 60 disposed over the expandable portion 44 are percutaneously inserted into a patient's vasculature over a guidewire 72. Once access is provided to the vasculature, the guidewire 72 can be advanced into the anatomy. For example, the guidewire 72 can be advanced into a femoral artery and along the aorta to the aortic valve and thereafter into the left ventricle.

Multiple guidewires having various properties can be used, including but not limited to heavy duty guidewires (e.g., Amplatz, Lunderquist). Advantageously, the use of a heavy duty and/or stiff guidewire can reduce kinking. Where multiple guidewires are used, a first guidewire can be preassembled into cannula 40 with a distal portion of the first guidewire exposed distally to the distal end of cannula 40. A second guidewire can be positioned in the patient as described herein, with a proximal portion of the second guidewire exposed extracorporeal to the patient. The proximal portion of the second guidewire, e.g., a portion that is in the patient, can be attached to the distal end of the first guidewire preassembled into cannula 40, and cannula 40 can be advanced along two connected guidewires to the desired position. In these embodiments, the connected first and second guidewires are configured to run coaxially within the drive shaft 26. Once the cannula 40 has been advanced to the desired position, the first and second guidewires are removed prior to activating drive shaft 26. Advantageously, the use of two or more guidewires can ease the threading and implantation process of the pump 10.

In certain techniques, the pump 10 can be delivered to a treatment site without the use of a guidewire. For example, once access has been provided to the vasculature, the pump 10 can be advanced to the descending aorta by pushing on the proximal end of the device to advance the distal end along the peripheral vessels (e.g., femoral or iliac), to track through a portion of the aorta (e.g., up to and around the aortic arch), to arrive at the aortic valve.

Optionally, the insertion site can be dilated prior to insertion of the cannula 40 and retainer sheath 60. After dilation, the cannula 40 and retainer sheath 60 assembly can be inserted into the vasculature. In other embodiments, a dilator tip 138 can be used, as shown in FIG. 7B. In FIG. 7B, dilator tip 138 is threaded over the distal end of guide wire 72. When a dilator is used, a separate pre-dilation step is not required. Rather, the cannula 40, sheath 60, and dilator tip 138 assembly can be inserted into the vasculature.

A distal end of the pump 10 can be advanced over the guidewire 72. For example, FIG. 3 illustrates that a cap 134 having an access port 136 can be provided at the distal end of the expandable portion 44 of cannula 40. The access port 136 is axially forward (or distal) of the lumen 130 that extends through the vane hub 122. Thus, the proximal end of the guidewire 72 can be advanced into the lumen 130 by moving the wire proximally through the port 136 axially along the length of the cannula 40. Thereafter, the pump 10 can be urged distally along the guidewire 72 into a position for treating the patient as in FIG. 9. Alternatively, the distal end of the guidewire can be urged into the proximal end pump 10 and distally through a lumen formed therein. This technique is particularly useful for the embodiments discussed where the valve 100 is disposed in the lumen 70 formed in the hub 22 of the impeller 20.

The pump 10 tracks over the guidewire 72 until the inlet 52 is disposed in a source of blood, such as in a chamber of a patient's heart. For example, the inlet 52 can be positioned in the left ventricle 500 and the outlet can be positioned in the aorta proximal of the aortic valve such that blood can be pumped from the ventricle through the conduit and into the systemic circulatory system. FIG. 9 illustrates that the proximal end of the expandable portion 44 of cannula 40 can be positioned in the ascending aorta 505. In other embodiments, outlet 54 of the expandable portion 44 of cannula 40 can be positioned in the aorta. In one embodiment where blood pump 10 is configured as an LVAD, the inlet 52 can reside in the left ventricle 500 of the heart and the outlet 54 can reside in the ascending aorta 505. In another embodiment, the expandable portion 44 of cannula 40 can be advanced until the impeller 20 is centered across the patient's aortic valve. In yet other embodiments, the cannula 20 can be advanced until the distal inlet 52 is positioned distally to the aortic valve and the proximal outlet 54 is proximal to the aortic valve. Still in a configuration of the pump where the cannula is made to be sufficiently long, the outlet 54 can reside in the descending aorta while the inlet 52 resides in the left ventricle, where the body of the cannula crosses the aortic valve.

As shown in one embodiment in FIG. 9, the pump 10 extends from the ascending aorta 505 into the femoral artery, from which it can exit the patient's body. Fluoroscopy or other imaging guidance can be used to monitor advancement and placement of the guidewire 72 and/or cannula 40 in the vasculature.

In one embodiment, the impeller 20 can be positioned toward the distal end 45 of cannula 40 which curves around through the aortic valve (not labeled) into the left ventricle 500 of the heart, while the flexible (and non-expandable) portion 30 of drive shaft 26, coupled to impeller 20, extends outside of the body of the patient (e.g., through the femoral artery) for connection to the drive motor.

C. Deploying the System

In one technique, after the pump 10 has been advanced, the expandable portion 44 can be deployed and expanded, such as by expanding the portion 44. An example of the expandable portion 44 in its expanded state is shown in FIG. 6B. In one technique, the expandable portion 44 of cannula 40 is expanded by retracting the retainer sheath 60, which allows the expandable portion 44 of cannula 40 to self-expand to the deployed configuration. The expansion of expandable portion 44 exposes the inlet 52 and the outlet 54 to blood.

A fluid seal can be provided where cannula 40 crosses a heart valve, e.g., the aortic valve, thereby significantly reducing any blood flow leaking through the heart valve around the outer wall of cannula 40. The seal can be formed by engagement between the outside wall of the cannula 40 and the aortic valve leaflets. In particular, the size of the cannula 40 when expanded can be greater than at least one state of the valve, e.g., the fully open state, such that the valve collapses around the cannula 40 in a manner that prevents fluid flow therebetween. In embodiments where cannula 40 is proximate to the aortic valve, the outer surface of the cannula 40 can be advantageously configured such that clinically significant abrasion of the aortic valve does not occur upon expansion. After expansion of expandable portion 44 of cannula 40, the guide wire 72 can be removed.

In one arrangement the, impeller blades 24 and vanes 124 are thereafter released from the stored configuration to a deployed configuration after the expandable portion of the cannula 44 is expanded. This can be achieved in any suitable way. For example, in one embodiment where impeller 20 is housed in the expandable portion 44 of cannula 40, the expansion of the cannula will remove the constraining force from impeller blades 24, and the blades will expand away from hub 22 and into the use condition simply from the energy stored when the blades are folded.

Alternatively, in some embodiments, the apparatus can include a storage housing 46 positioned around the impeller 20, as shown in FIG. 8B. Where impeller 20 is housed within storage housing 46, the impeller can be pushed from its stored position by applying a small force to drive shaft 26 while holding the housing 46 at a fixed location. Once advanced out of storage housing 46 and into the expandable portion 44 of cannula 40, the blades 24 of impeller 20 can unfold to the use or operation condition, as shown in FIG. 8A. In one embodiment, the step of releasing the impeller 20 from the stored configuration to a deployed configuration can include axially sliding the storage housing 46 in a proximal direction until at least a portion of the impeller 20 (e.g., a portion including the blades 24) is released from the storage housing 46. In another embodiment, the step of releasing impeller 20 from the stored configuration to a deployed configuration can include axially sliding the impeller 20 in a distal direction until at least a portion of the impeller 20 (e.g., a portion including the blades 24) is released from the storage housing 46. Hydrodynamic forces and centripetal force from spinning about the hub can also cause impeller blades 24 to further transform into their operating configuration when in use.

In embodiments including stator vane assembly 120, expansion of expandable portion 44 will also remove the constraining force from stator vanes 124, thus permitting the stator vanes 124 to be deployed away from the vane hub 122 and allowing their tips to be disposed adjacent to and in one embodiment, be in contact with an inner surface of the cannula. In some embodiments that include a storage housing 46, the steps of deploying the impeller 20 and deploying the vane assembly 120 can include moving the impeller 20 and vane assembly 120 together axially in a longitudinally distal direction until at least a portion of the impeller 20 and the vane assembly 120 (e.g., blades 24 and vanes 124, respectively) are released from the storage housing 46.

D. Operating the System

In some cases, it is desirable to infuse a fluid into the pump 10 after the pump has been deployed. For example, the pump 10 can include a system for collecting, purging, or otherwise managing contaminants or debris that can be generated by or come into contact with the working components. As discussed above, the lumen 70 provides access from the proximal end of the pump 10 to the distal end of the impeller 20, as shown in FIG. 2A. The nature of the purge system is not critical, but can take the form of the system disclosed in FIGS. 2 and 7 and corresponding text of U.S. Patent Publication No. 2006/0161095, which is hereby incorporated by reference herein. In one technique, as illustrated in FIGS. 8A-8B, the lumen 70 is pressurized with saline prior to operation of the pump 10. As discussed above, the pressurized fluid flows distally into the lumen 70 and cause the valve 100 to close when pressure in the lumen 70 exceeds back pressure from the patient's vasculature. Flow of the saline or other fluid from the proximal end toward the distal end of the lumen can also exit the lumen through the opening 88 to enter the bearing housing 84 to assist in bearing function. In some cases, the fluid can at least partially form a hydrodynamic bearing or can be used to cool the bearings.

Once the device is positioned and the expandable portion 44 of cannula 40 and the impeller 20 are expanded to their respective deployed conditions, the deployment tool can be removed and the relative positions of the storage housing 46 and/or the sheath 60 can be fixed. A drive unit can be connected to the blood pump 10 and treatment can be initiated. The impeller 20 can then be operated to pump blood through at least a portion of the cannula 40.

In operation, the impeller 20 can rotate about a longitudinal axis of the drive shaft 26 to pull fluid in to the expandable portion 44 through inlet 52 and out through outlet 54. Inlet 52 and struts 56 at the distal end of expandable portion 44 can allow substantially unrestricted flow of blood into blood pump 10, where it is driven by impeller 20 proximally through the discharge struts 58 and outlet 54 at the proximal end 47 of expandable portion 44.

In embodiments that include a vane assembly 120, the vane assembly 120 can be configured not to rotate along with the impeller 20. As described herein, the vane assembly 120 advantageously provides lateral stability to the impeller 20 and helps to keep the impeller 20 centered within expandable portion 44 while in operation. The blood pump 10 can be operated at any desired rate, such as at a generally cardiac rate or at a generally subcardiac rate. In some embodiments, the blood pump 10 is capable of operating at a rate in the range of from about 2 L/min to about 5 L/min under typical physiological pressure, e.g., 90 mm Hg. In other embodiments, the blood pump 10 can be operated at a rate in the range of from about 1 L/min to about 3 L/min against typical physiological pressure, e.g., 90 mm Hg.

E. Removal of the System

Subsequently, the apparatus can be removed from the patient's vasculature. For example, the apparatus can be removed when the patient recovers and can be weaned from the necessity of using blood pump intervention.

Removal of the pump 10 can be accomplished in a manner similar to the preparation of the pump for insertion into the body. For example, the expandable components of the pump 10 can be compressed in a similar manner. The impeller 20 can be compressed by urging the impeller 20 into the storage housing 46 or into non-expandable portion 42 of cannula 40. The expandable portion 44 of cannula 40 can be compressed by urging the proximal end of the expandable portion 44 of cannula 40 into the distal end of the retainer sheath 60.

In some embodiments, a retraction tool can be used for guiding or retracting the expandable portion 44 of cannula 40 into the sheath 60. The retraction tool can be similar in structure to the compression tool and/or deployment tool described herein. As described herein, retainer sheath 60 is configured, in one embodiment, to be non-deformable and/or non-expandable. For example, retainer sheath 60 can have a generally fixed diameter. The step of urging the expandable portion 44 of cannula 40 into retainer sheath 60 can be accomplished in a variety of ways. For example, the generally axial rigidity of a guidance aid (e.g., the proximal extents of the connectors 57, axially extending ribs, and/or second region 59) can cause the expandable portion 44 of the cannula 40 to collapse. In some embodiments, the guidance aids are generally flat long and narrow in shape and may be aligned axially between the proximal and distal ends of the expandable portion 44 to thus direct the expandable portion 44 in the axial direction into retainer sheath 60. In embodiments where the guidance aids connect the adjacent rings 51, the guidance aids can facilitate pulling each ring 51 into the sheath 60. As the expandable portion 44 collapses, blood within the expandable portion 44 between the inlet 52 and outlet 54 will be flushed distally out of the inlet 52.

As described herein with respect to FIGS. 15A, 15B, and 16, the expandable portion 44 of cannula 40 can include a plurality of circumferential rings 51 and a plurality of guidance aids, which can be configured as connectors 57 attached to one or more circumferential rings 51. In these embodiments, the step of guiding the expandable portion 44 of cannula 40 into the sheath 60 can include using the plurality of connectors 57 to guide the expandable portion 44 of cannula 40 in a direction generally parallel to each connector 57 and into the sheath 60. Advantageously, this step can be performed without the use of a funnel and/or with a non-deformable, non-expandable, and/or generally fixed-diameter sheath 60. By eliminating the need for a distally enlarged structure like a funnel, the pump 10 can be configured to enter a small vessel, such as a vessel accessible close to the surface. As a result, the pump 10 can applied in the catheterization lab by a cardiologist and surgical application is not required. Those of ordinary skill in the art may appreciate that in use, blood may be likely to pool near the funnel, increasing the risk of thrombus. Therefore, another advantage of funnel-less removal can be a decreased risk of thrombus.

As shown in FIG. 17 and as described further herein, the expandable portion 44 of cannula 40 can include a plurality of circumferential rings 51, a first layer 50 of a first polymer at least partially coating an exterior of the circumferential rings 51, and at least one region 59 of a second polymer different from the first polymer that overlies the first polymer layer and connects at least a first circumferential ring to a second circumferential ring. In these embodiments, the second polymer region 59 can function as a guidance aid for the expandable portion 44. The step of guiding the expandable portion 44 of cannula 40 into the sheath 60 can include using the second polymer region 59 to guide the expandable portion 44 of cannula 40 axially into the sheath 60. Advantageously, this step can be performed without the use of a funnel and/or with a non-deformable, non-expandable, and/or generally fixed-diameter sheath 60. Thus, the second polymer region 59 can be configured to enable the pump 10 be minimally invasively applied, as discussed above.

F. Use as a Right Ventricular Assist Device

In addition to use as an LVAD, the device described herein can also be used as a right ventricular assist device (RVAD) in a manner similar to that described above. When the device is used as an RVAD, the device can be inserted into the vasculature via a peripheral vein, such as the femoral, axillary, subclavian, or the jugular vein, through the vena cava and into the patient's heart.

The device can be inserted to a position where the distal end of the expandable portion 44 of cannula 40 is at a location distal to the patient's pulmonary valve (e.g., inside the pulmonary artery) and the proximal end of the expandable portion 44 of cannula 40, e.g., is at a location proximal to the patient's pulmonary valve (e.g., inside the right ventricle). For example, a portion of the proximal end of the expandable portion 44 of cannula 40 can reside in the patient's right ventricle and the blood flow outlet of the system can be disposed in the pulmonary artery. The inlet of the system, which can be adjacent to the proximal end of the expandable portion 44 of cannula 40, would be disposed in the patient's right ventricle, right atrium, or vena cava. Advantageously, when the device is used as an RVAD, it can be configured so that the flow is reversed, such that the conduit at the proximal end of the expandable portion 44 of cannula 40 can operate as a flow inlet, and the conduit at the distal end of the expandable portion 44 of cannula 40 can operate as a flow outlet. Such a configuration can be achieved by a variety of methods, such as by reversing the pitch of the impeller blades. In some embodiments, the impeller can operate at a reduced flow rate when configured as an RVAD. Advantageously, other features of the impeller, such as the bearings, drive shaft, drive cable, and the like, may not need to be modified from the LVAD configuration. Other applications of the device described herein include providing additional blood flow to other organs, assisting the heart during operations and the like.

Applications of the improved fluid pump design described herein are not limited to ventricular assist devices. The improved cannula and impeller designs are useful for any application where a stored configuration having a reduced diameter is useful for locating the pump at a desired location. For example, a fluid pump operating underground can be introduced into a pipe, channel or cavity through an opening of lesser diameter, and operate at a diameter greater than that of the opening used. Applications of an impeller deploying within an expandable portion of a cannula include a collapsible fire hose with an integral booster pump, a collapsible propeller, a biomedical pump for a biological fluid, and the like.

Although the invention herein has been described with reference to particular embodiments, it is to be understood that these embodiments are merely illustrative of the principles and applications of the present invention. It is therefore to be understood that numerous modifications can be made to the illustrative embodiments and that other arrangements can be devised without departing from the spirit and scope of the present invention as defined by the appended claims.

What is claimed is:

1. A pump, comprising:
   an elongated cannula having a proximal portion and a distal portion;
   an impeller positioned in the elongated cannula and configured to rotate about an axis; and
   an expandable vane assembly positioned in the elongated cannula about the axis adjacent the impeller and having a deployed configuration and a stored configuration, the vane assembly comprising a vane, the vane in the deployed configuration extending away from the axis, the vane in the stored configuration compressed inwardly towards the axis relative to the deployed configuration.

2. The pump of claim 1, wherein the vane is configured to expand to the deployed configuration by release of strain stored in the vane.

3. The pump of claim 1, wherein the distal portion of the elongated cannula includes an expandable portion having an expanded configuration and a collapsed configuration, the vane assembly disposed in the expandable portion.

4. The pump of claim 3, wherein the vane assembly is configured to move from the stored configuration to the deployed configuration when the expandable portion moves from the collapsed configuration to the expanded configuration.

5. The pump of claim 3, wherein a free end of the vane contacts an inner wall of the expandable portion when the vane assembly is in the deployed configuration.

6. The pump of claim 5, wherein the vane assembly is positioned distally of the impeller.

7. The pump of claim 6, wherein the vane assembly is configured to maintain the impeller substantially centered in the expandable portion of the cannula during operation of the pump.

8. The pump of claim 6, wherein the impeller comprises a blade, and wherein the vane assembly is configured to maintain a consistent clearance between a tip of the blade and the inner wall of the expandable portion of the elongated cannula during operation of the pump.

9. The pump of claim 1, wherein the vane assembly comprises:
a vane hub; and
a plurality of vanes supported by the vane hub, each of the vanes having a proximal end attached to the vane hub and a distal end,
the vanes in the deployed configuration of the vane assembly extending away from the vane hub, and the vanes in the stored configuration of the vane assembly being compressed so as to move the distal ends of the vanes towards the vane hub.

10. The pump of claim 1, wherein the vane is oriented at an angle to a direction of blood flow through the elongated cannula.

11. The pump of claim 10, wherein the vane is angled to induce a circumferential velocity component to the blood flow.

12. The pump of claim 1, wherein the vane assembly is mechanically coupled to the impeller along the axis but does not rotate with the impeller.

13. The pump of claim 12, wherein the impeller comprises a hub and a blade, the vane assembly mounted to a distal end of the impeller.

14. The pump of claim 13, further comprising:
a lumen extending axially through the hub of the impeller and the vane assembly, the lumen adapted to receive a guidewire therethrough for guiding the impeller and vane assembly to a target site in the anatomy of a patient; and
a seal positioned within the lumen, the seal configured to prevent a flow of fluid into the lumen after the guidewire is removed.

15. The pump of claim 14, wherein the seal is disposed in a portion of the lumen that is within the vane assembly.

16. The pump of claim 3, further comprising a retainer sheath disposed over a portion of the elongated cannula, the retainer sheath configured to cause the expandable portion to move from the collapsed configuration to the expanded configuration by moving the retainer sheath proximally relative to the expandable portion such that the expandable portion self-expands to the expanded configuration, and
wherein the retainer sheath is configured to cause the expandable portion to move from the expanded configuration to the collapsed configuration by moving the retainer sheath distally over the expandable portion to collapse the expandable portion to the collapsed configuration.

17. A pump, comprising:
an elongated cannula having a proximal portion and a distal portion, the distal portion comprising an expandable portion;
an impeller disposed in the expandable portion;
a sheath having a generally non-expanding distal portion; and
one or more guidance aids configured to facilitate retraction of the expandable portion into the distal portion of the sheath when relative motion is provided between the distal portion of the sheath and the expandable portion.

18. The pump of claim 17, wherein the one or more guidance aids is configured such that relative axial motion between the distal portion of the sheath and the expandable portion applies a force having a radial component to a proximal end of the one or more guidance aids to induce radial collapse of the expandable portion into the sheath.

19. The pump of claim 17, wherein the expandable portion comprises a plurality of undulating circumferential rings and the guidance aid comprises an axial member coupled at a distal end with a portion of one of the circumferential rings and a proximal end disposed proximally of the distal end.

20. The pump of claim 19, wherein the proximal end of the axial member is coupled with an apex of a proximal circumferential ring and the distal end of the axial member is coupled with an apex of a distal circumferential ring.

21. The pump of claim 19, wherein the axial member connects an apex of one circumferential ring to a side of an adjacent circumferential ring.

22. The pump of claim 17, wherein the one or more guidance aids comprises a polymeric rib structure disposed axially along the expandable portion.

23. A method of pumping blood in a patient, comprising:
inserting a blood pump into the patient, the blood pump comprising an elongated cannula, an impeller positioned in the elongated cannula, and an expandable vane assembly positioned in the elongated cannula near the impeller, the expandable vane assembly having a deployed configuration and a stored configuration, the vane assembly comprising a vane;
positioning the blood pump in the patient so that the impeller is at a desired location;
expanding the expandable vane assembly from the stored configuration to the deployed configuration within the elongated cannula; and
rotating the impeller about an axis to pump blood through the elongated cannula.

24. The method of claim 23, wherein the impeller is an expandable impeller having a deployed configuration and a stored configuration, wherein a distal portion of the elongated cannula includes an expandable portion having an expanded configuration and a collapsed configuration, the vane assembly disposed in the expandable portion, the method further comprising:
expanding the expandable impeller from the stored configuration to the deployed configuration; and
expanding the expandable portion from the collapsed configuration to the expanded configuration.

25. The method of claim 24, further comprising:
collapsing the expandable vane assembly from the deployed configuration to the stored configuration such that the vane is compressed inwardly towards the axis relative to the deployed configuration;
collapsing the expandable impeller from the deployed configuration to the stored configuration; and
collapsing the expandable portion of the elongated cannula from the expanded configuration to the stored configuration.

26. The method of claim 25, wherein the blood pump comprises a retainer sheath disposed about the elongated cannula, the method further comprising:
retracting the retainer sheath proximally relative to the expandable portion of the elongated cannula to urge the expandable portion out of the retainer sheath to expand the expandable portion, the expandable impeller, and the expandable vane assembly; and
advancing the retainer sheath distally over the expandable portion to collapse the expandable portion, the expandable impeller, and the expandable vane assembly.

27. The method of claim 24, wherein the impeller comprises a blade, the method further comprising maintaining a consistent clearance between a tip of the blade and an inner wall of the expandable portion.

28. The method of claim 27, wherein maintaining the consistent clearance comprises contacting a free end of the vane with the inner wall of the expandable portion.

29. The method of claim 24, wherein positioning the blood pump in the patient comprises positioning the expandable portion of the elongated cannula such that at least part of the expandable portion is disposed in the right ventricle of the patient.

* * * * *